United States Patent
Umemoto et al.

[11] Patent Number: 5,892,035
[45] Date of Patent: Apr. 6, 1999

[54] PROCESS FOR PREPARING N,N'-DIFLUORODIAZONIABICYCLOALKANE SALT, INTERMEDIATE THEREFOR

[75] Inventors: Teruo Umemoto; Masayuki Nagayoshi; Ginjiro Tomizawa; Kenji Adachi, all of Tsukuba, Japan

[73] Assignee: Daikin Industries Ltd., Osaka, Japan

[21] Appl. No.: 809,932

[22] PCT Filed: Aug. 2, 1996

[86] PCT No.: PCT/JP96/02183

§ 371 Date: May 15, 1997

§ 102(e) Date: May 15, 1997

[87] PCT Pub. No.: WO97/06170

PCT Pub. Date: Feb. 20, 1997

[30] Foreign Application Priority Data

Aug. 3, 1995 [JP] Japan ................................. 7-198814
Oct. 31, 1995 [JP] Japan ................................. 7-283343

[51] Int. Cl.⁶ .......................... C07D 487/08; C07B 39/00
[52] U.S. Cl. ......................... 544/351; 540/472; 540/556
[58] Field of Search ............... 544/351; 540/472, 540/556

[56] References Cited

U.S. PATENT DOCUMENTS 5,367,071 11/1994 Syvret ..................... 544/351
5,459,267 10/1995 Ross ........................ 544/351

FOREIGN PATENT DOCUMENTS 0 657457  6/1995  European Pat. Off. .
7-233167  9/1995  Japan .

OTHER PUBLICATIONS

Banks, JCS Chem Comm 1992, 595.
Stavber, Tet. Letters 35, 1105 (1994).
Umemoto, B. C. S. J. 64, 1081 (1991).

*Primary Examiner*—Mark L. Berch
*Attorney, Agent, or Firm*—Birch, Stewart, Kolasch & Birch, LLP

[57] ABSTRACT

A process for preparing a N,N'-difluorodiazoniabicycloalkane salt of the formula:

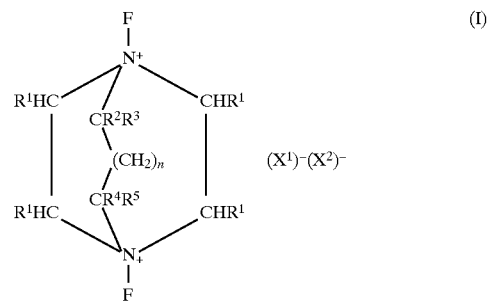

by reacting a corresponding diazabicycloalkane or diazabicycloalkane Brønsted acid salt and fluorine in the presence of a Brønsted acid or in the presene or absence of a base, by reacting a corresponding N,N'-difluorodiazoniabicycloalkane salt and an acid or salt, by reacting a corresponding diazabicycloalkane and fluorine in the presence of a Brønsted acid and then reacting an intermediate product and an acid or salt, or by reacting a corresponding diazabicycloalkane Brønsted acid salt and fluorine in the presence or absence of a base and then reacting an intermediate product and an acid or salt.

16 Claims, No Drawings

PROCESS FOR PREPARING N,N'-DIFLUORODIAZONIABICYCLOALKANE SALT, INTERMEDIATE THEREFOR

This application is a 371 of PCT/JP96/02183, filed Aug. 2, 1996.

FIELD OF THE INVENTION

The present invention relates to a process for preparing a N,N'-difluorodiazoniabicycloalkane salt, an intermediate useful for synthesizing such the salt, a product and use of the product.

The N,N'-difluorodiazoniabicycloalkane salts are useful as an electrophilic fluorinating agent for organic compounds (see U.S. Pat. No. 5,367,071, EP-A-0 657 457 and JP-A-7-233167).

PRIOR ART

The following processes have been developed for the preparation of the N,N'-difluorodiazoniabicycloalkane salts:

(1) A 1-hydro-4-aza-1-azoniabicycloalkane salt is fluorinated with fluorine ($F_2$) in the presence of an alkali metal salt ($LiOSO_2CF_3$) (see U.S. Pat. No. 5,367,071);

(2) A 1,4-diazabicycloalkane is reacted with a twice molar amount of a Lewis acid ($BF_3$, $PF_5$ or $SO_3$), and then fluorinated with $F_2$ (see EP-A-0 657 457, Examples 3, 4 and 5);

(3) A 1,4-diazabicycloalkane is reacted with an equimolar amount of a Lewis acid ($BF_3$), followed by fluorination with $F_2$ in the presence of an alkali metal salt ($NaBF_4$) and a monofluorinated intermediate is obtained. Then, this intermediate is treated with 100% $F_2$ in a sealed reactor under reduced pressure (20 mmHg) (see EP-A-0 657 457, Examples 1 and 2).

(4) A 1,4-diazabicycloalkane is reacted with a trialkylsilylester ($Me_3SiOSO_2CF_3$), followed by fluorination with $F_2$ (see EP-A-0 657 457, Example 6).

(5) A 1,4-diazabicycloalkane-monotrifluoroborane is reacted with perfluorobutyl chloride in the presence of $NaBF_4$ and 1-perfluorobutyl-1,4-diazoniabicycloalkane-trifluoroborane tetrafluoroborate is obtained. Then, this tetrafluoroborate is fluorinated with $F_2$ in the presence of $NaBF_4$ (see EP-A-0 657 457, Example 7).

However, these recently developed processes are not industrially advantageous processes since they have the following material drawbacks:

In the process (1), the product is obtained as a mixture with the unreacted raw materials, and a metal fluoride which is another product of the reaction induces the decomposition of the desired product. Therefore, it is difficult to isolate the desired product in the pure form. Furthermore, it is difficult to remove the insoluble metal salt from the product having the low solubility.

In the process (2), a large amount of the solvent is necessary, for example, 25 ml of $CH_3CN$ per 1 mmol of the diazabicycloalkane, in particular when a N,N'-difluorodiazoniabicycloalkane bis(tetrafluoroborate) which is a useful fluorinating agent is prepared. The yield of the product is low. Furthermore, the product is obtained as a mixture of the raw material, its monofluoride and the desired product and the obtained mixture is a hygroscopic solid and decomposes through moisture absorption. Therefore, the purification of the product is impossible.

The process (3) is highly dangerous since fluorination is carried out in a sealed reactor under reduced pressure ($F_2$ pressure of 20 mmHg) with contacting extremely dangerous 100% $F_2$ gas, which may ignite and explode when it comes in contact with the organic solvent around atmospheric pressure to increase the yield, to the reaction solution in the organic solvent.

The process (4) uses the expensive trialkylsilyl ester, and is also dangerous since a large amount of volatile trialkylsilyl fluoride which is generated as a by-product reacts with $F_2$ vigorously and may explode.

The process (5) must use the expensive perfluoroalkanoyl fluoride, and requires a large amount of the solvent like the process (2). The yield is low. Furthermore, the product after post-treatment is a mixture of the monofluoride and the desired product in a ratio of 7:10, and therefore, the purification of the product is difficult.

SUMMARY OF THE INVENTION

As the result of diligent studies for solving the above problems, a novel process has been found which can prepare a desired product of high purity by fluorinating a diazabicycloalkane in the presence of a Brønsted acid, and if necessary treating the product with an acid and the like, and the present invention has been completed.

That is, the objects of the present invention are to solve the above described problems, and to provide a process for easily preparing a N,N'-difluorodiazoniabicycloalkane salt of high purity, which is a useful fluorinating agent, from a cheap raw material in a high yield, a useful intermediate for the synthesis of said salt, a desired product and use of the desired product.

In a broad sense, the present invention provides a process for preparing a N,N'-difluorodiazoniabicycloalkane salt of the formula (I):

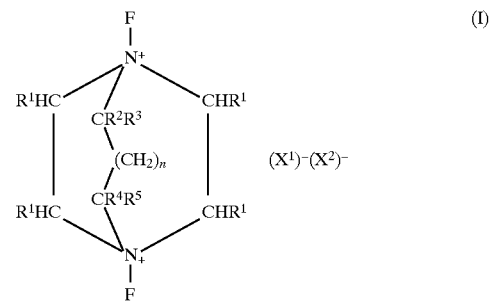

wherein $R^1$, $R^2$, $R^3$, $R^4$ and $R^5$ represent independent of each other a hydrogen atom, a $C_1$–$C_6$ alkyl group, an aryl group, a $C_1$–$C_6$ alkyl group-substituted aryl group or an aryl group-substituted $C_1$–$C_6$ alkyl group, $(X^1)^-$ and $(X^2)^-$ represent independent of each other a conjugated base of a Brønsted acid or together form a single conjugated base of a Brønsted acid, and n is 0, 1 or 2.

The above aryl group is preferably a $C_6$–$C_{10}$ aryl group.

DETAILED DESCRIPTION OF THE INVENTION

In the first embodiment of the present invention, a N,N'-difluorodiazoniabicycloalkane salt of the formula (I) is prepared by reacting fluorine ($F_2$) and a diazabicycloalkane of the formula (II):

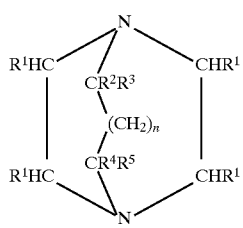

(II)

wherein $R^1$, $R^2$, $R^3$, $R^4$, $R^5$ and n are the same as defined above, in the presence of a Brønsted acid.

The diazabicycloalkane of the formula (II) may be a known compound and readily available or easily prepared by an analogous method to those for the preparation of the known compounds (see JP-A-6-25247 and U.S. Pat. No. 5,086,178).

In particular, the compound of the formula (II) in which $R^1$, $R^2$, $R^3$, $R^4$ and $R^5$ are all hydrogen atoms and n is 0 (1,4-diazabicyclo[2.2.2]octane) is commercially produced and sold under the trade name of DABCO (available from Air Products and Chemicals, Inc.) and the like for the preparation of polyurethane foams, elastomers, epoxy resins, polyacrylonitrile, polyethylene, and their analogous materials.

The above process of the present invention is characterized in that the fluorination reaction is carried out in the presence of a Brønsted acid.

When the N,N'-difluorodiazoniabicycloalkane salt of the formula (I) in which the anions $(X^1)^-$ and $(X^2)^-$ are the same anion is prepared, an acid is used, while when the anions $(X^1)^-$ and $(X^2)^-$ are different, at least one acid is used.

Preferred Brønsted acids are those having the acidity equal to or larger than that of trifluoroethanol known as a weak acid (having an acid dissociation constant pKa of 12.4. see J. Org. Chem., 32, 1217 (1967)). Brønsted acids having pKa equal to or smaller than pKa of acetic acid, that is, 4.6 are more preferable for performing the reaction in a good yield.

Preferable examples of the Brønsted acid having pKa in the range between about 12.4 and 4.6 are halogenated alcohols (e.g. trifluoroethanol, chlorodifluoroethanol, dichlorofluoroethanol, trichloroethanol, tetrafluoropropanol, pentafluoropropanol, hexafluoroisopropanol, octafluoropentanol, hexafluoro-t-butanol, chlorooctafluoro-t-butanol, etc.), halogen-oxoacids (e.g. hypochlorous acid, hypobromous acid, hypoiodous acid, etc.), boric acid, carbonic acid, silicic acid, and the like.

Many known inorganic and organic acids are exemplified as the Brønsted acids having pKa of 4.6 or less. Preferable examples are hydrogen halides; oxoacids of phosphorus (e.g. phosphoric acid, metaphosphoric acid, pyrophosphoric acid, diphosphoric acid, triphosphoric acid, tetraphosphoric acid, polyphosphoric acid, phosphorous acid, hypophosphorous acid, etc.); oxoacids of nitrogen (e.g. nitric acid, nitrous acid, etc.); oxoacids of sulfur (e.g. sulfuric acid, sulfurous acid, thiosulfuric acid, dithionic acid, pyrosulfuric acid, disulfuric acid, polythionic acid, etc.); oxoacids of selenium or tellurium (e.g. selenic acid, selenious acid, tellurous acid, etc.); halosulfonic acids (e.g. fluorosulfonic acid, chlorosulfonic acid, etc.); monoalkylsulfuric acids (e.g. monomethylsulfuric acid, monoethylsulfuric acid, etc.); alkanesulfonic acids (e.g. methanesulfonic acid, ethanesulfonic acid, propanesulfonic acid, butanesulfonic acid, etc.); haloalkanesulfonic acids (e.g. trifluoromethanesulfonic acid, difluoromethanesulfonic acid, trichloromethanesulfonic acid, trifluoroethanesulfonic acid, nonafluorobutanesulfonic acid, etc.); alkane- or haloalkanedisulfonic acids (e.g. methanedisulfonic acid, ethanedisulfonic acid, tetrafluoroethanedisulfonic acid, propanedisulfonic acid, butanedisulfonic acid, perfluorobutanedisulfonic acid, etc.); arenesulfonic acid (e.g. benzenesulfonic acid, pentafluorobenzenesulfonic acid, toluenesulfonic acid, nitrobenzenesulfonic acid, dinitrobenzenesulfonic acid, bromobenzenesulfonic acid, etc.); arenedisulfonic acids (e.g. benzenedisulfonic acid, naphthalenedisulfonic acid, etc.); alkanoic or haloalkanoic acids (e.g. formic acid, acetic acid, propionic acid, trifluoroacetic acid, trichloroacetic acid, pentafluoropropionic acid, etc.); oxalic acid; alkane- or haloalkanedicarboxylic acids (e.g. methanedicarboxylic acid, ethanedicarboxylic acid, propanedicarboxylic acid, tetrafluoroethanedicarboxylic acid, perfluoropropanedicarboxylic acid, perfluorobutanedicarboxylic acid, etc.); alkanediphosphonic acids (e.g. methanediphosphonic acid, etc.), compounds comprising hydrogen halides and Lewis acids (e.g. $HBF_4$, $HBCl_4$, $HBCl_3F$, $HB_2F_7$, $HAlF_4$, $HAlCl_4$, $HAlCl_3F$, $HAsF_4$, $HAsF_6$, $HAsCl_3F$, $HAs_2F_{11}$, $HPF_4$, $HPF_6$, $HSbF_4$, $HSbCl_4$, $HSbF_6$, $HSbCl_5F$, $HSbCl_6$, $HSb_2F_7HSb_2F_{11}$, $HSiF_5$, $H_2SiF_6$, $H(CF_3)_3BF$, $H(C_6H_2F_3)_3BF$, $H(C_6F_5)BF$, $HNbF_6$, $HTaF_6$, $HTeF_7$, $HTiF_5$, $HVF_6$, $HZrF_5$, etc.); oxoacids of halogens (e.g. $HClO_3$, $HClO_4$, $HBrO_4$, $HIO_3$, $HIO_4$, etc.); tetraarylboric acids, (e.g. tetra[di(trifluoromethyl)phenyl]boric acid, etc.); and the like.

Among the above exemplified Brønsted acids, those having pKa smaller than pKa of hydrogen fluoride (HF), that is, 3.17 are particularly preferable for preparing the highly pure N,N'-difluorodiazoniabicycloalkane salt of the formula (I) in a high yield.

The Brønsted acid used in the present invention may be used in the form of a complex with ethers (e.g. diethyl ether, dibutyl ether, t-butyl methyl ether, dimethyl ether, etc.); sulfides (e.g. dimethyl sulfide, diethyl sulfide, etc.); water; alcohols (e.g. methanol, ethanol, propanol, etc.); nitriles (e.g. acetonitrile, propionitrile, etc.); carboxylic acids (e.g. formic acid, acetic acid, etc.); and the like. The Brønsted acid may be used in the form of an aqueous solution.

When the Brønsted acid is a monobasic one, the amount of the acid is at least 0.9 mole per 1 mole of the diazabicycloalkane of the formula (II). Preferably, the amount of the Brønsted acid is at least 1 mole, more preferably at least 1.5 moles in view of the yield. When the acid dissociation constant pKa is 4.6 or less, the amount of the Brønsted acid is between 0.9 and 5 moles, more preferably between 1 and 3 moles in view of the yield or costs. For performing the reaction at high efficiency and yield, the amount of the Brønsted acid is preferably between 1.5 and 2.5 moles, in particular between 1.8 and 2.2 moles.

When the Brønsted acid is a dibasic one, the amount of the acid is at least 0.45 mole per 1 mole of the diazabicycloalkane of the formula (II). Preferably, the amount of the Brønsted acid is at least 0.5 moles to obtain the product in the high yield. When the acid dissociation constant pKa is 4.6 or less, the amount of the Brønsted acid is between 0.45 and 5 moles, more preferably between 0.5 and 3 moles in view of the yield or costs. For performing the reaction at high efficiency and yield, the amount of the Brønsted acid is preferably between 0.75 and 2.5 moles, in particular between 0.9 and 2.2 moles.

When the N,N'-difluorodiazoniabicycloalkane salt of the formula (I) in which $(X^1)^-$ and $(X^2)^-$ together form a single conjugated base of a Brønsted acid is prepared, the amount of the dibasic acid is preferably in the range between 0.75 and 1.3 moles, more preferably between 0.9 and 1.2 moles per 1 mole of the diazabicycloalkane of the formula (II).

The Brønsted acid may be used also as a solvent for the reaction as explained below when it is a relatively weak liquid acid, for example, the halogenated alcohols such as trifluoroethanol, trichloroethanol, pentafluoropropanol, hexafluoroisopropanol, tetrafluoropropanol, nonafluoro-t-butanol, etc.; hydrogen fluoride; or the alkanoic- or haloalkanoic acids such as formic acid, acetic acid, trifluoroacetic acid, etc.

The fluorine ($F_2$) used in the present invention is in general a fluorine gas. While the fluorine gas may be used without dilution, in general, it is preferable to use the fluorine gas diluted with an inert gas so that the volume of the inert gas is between 99.9% and 50% for controlling the vigorous reaction.

The inert gas may be nitrogen, helium, argon gas, etc.

In general, the reaction proceeds with blowing the fluorine gas or diluted fluorine gas in or on the reaction mixture. The reaction gas may be circulated for increasing the reaction efficiency. Alternatively, the reaction may proceed with supplying the fluorine gas or diluted fluorine gas in the reactor under subatmospheric pressure.

The amount of the fluorine may not be uniformly determined since it varies with the introduction manner, reaction solvent, reaction temperature, reactor, and the like, but can be easily determined by a person skilled in the art with aiming at an amount required for the absorption of the fluorine to substantially cease.

The reaction in the process of the present invention is preferably carried out in a solvent.

Preferred examples of the solvent are $C_2$–$C_5$ nitriles (e.g. acetonitrile, propionitrile, butyronitrile, isobutyronitrile, valeronitrile, isovaleronitrile, etc.); $C_1$–$C_8$ halohydrocarbons (e.g. methylene chloride, chloroform, carbon tetrachloride, chlorotrifluoromethane, bromotrifluoromethane, dichloroethane, tetrachloroethane, tetrafluoroethane, chlorotrifluoroethane, trichlorotrifluoroethane, perfluorobutane, perfluorohexane, perfluorooctane, etc.); water; $C_1$–$C_5$ alcohols or halogenated alcohols (e.g. methanol, ethanol, propanol, isopropanol, butanol, isobutanol, sec.-butanol, t-butanol, trifluoroethanol, trichloroethanol, hexafluoroisopropanol, pentafluoropropanol, tetrafluoropropanol, hexafluorobutanol, nonafluoro-t-butanol, octafluoropentanol, nonafluoropentanol, etc.); hydrogen fluoride; phosphoric acid; $C_1$–$C_4$ alkanoic or haloalkanoic acids (e.g. formic acid, acetic acid, propionic acid, butanoic acid, trifluoroacetic acid, pentafluoropropionic acid, heptafluorobutanoic acid, etc.); and mixtures thereof.

Among them, the $C_2$–$C_5$ nitriles, $C_1$–$C_5$ halogenated alcohols, $C_1$–$C_4$ alkanoic acids or haloalkanoic acids or their mixtures are preferable for performing the reaction effectively and obtaining the product in the high yield.

The reaction temperature is usually in the range between about −100° C. and about +80° C. Preferably, the reaction temperature is in the range between −80° C. and +50° C. for performing the reaction at the high yield of the product.

When the amount of the Brønsted acid is less than 2 moles per 1 mole of the diazabicycloalkane of the formula (II), it may be preferable in some cases to supplement the acid in the reaction liquid or mixture after the reaction step so that the total amount of the acid used in the reaction and the supplemented acid becomes 2 moles or more for improving the stability of the produced N,N'-difluorodiazoniabicycloalkane salt of the formula (I) or increasing the yield after isolation and purification.

When the used Brønsted acid is a dibasic one and therefore the N,N'-difluorodiazoniabicycloalkane salt of the formula (I) in which $(X^1)^-$ and $(X^2)^-$ together form the single conjugated base of the Brønsted acid is prepared, and the amount of the acid used in the reaction step is less than 1 mole, it is preferable to supplement the acid in the reaction liquid or mixture after the reaction step so that the total amount of the acid used in the reaction step and the supplemented acid becomes 1 mole or more or at most 1.1 moles.

After the supplement of the acid, the reaction mixture is posttreated by any conventional method.

In the second embodiment of the present invention, a N,N'-difluorodiazoniabicycloalkane salt of the formula (I) is prepared by reacting fluorine and a Brønsted acid salt of a diazabicycloalkane of the formula (III):

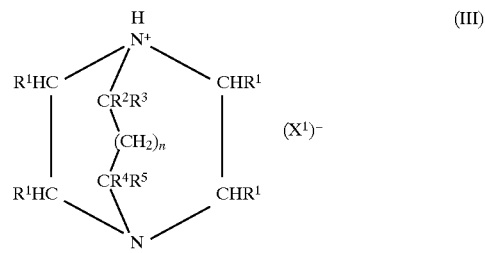

wherein $R^1$, $R^2$, $R^3$, $R^4$, $R^5$, n and $(X^1)^-$ are the same as defined above, in the presence or absence of a Brønsted acid.

The Brønsted acid salt of the diazabicycloalkane of the formula (III) used as the starting material in the above reaction is readily prepared by mixing the diazabicycloalkane of the formula (II) and an equimolar amount of the above Brønsted acid.

When the compound of the formula (I) in which $(X^1)^-$ and $(X^2)^-$ independently represent the same or different conjugated bases of the Brønsted acids is prepared, the above reaction is preferably carried out in the presence of the Brønsted acid. When the compound of the formula (I) in which $(X^2)^-$ is a fluoride or HF-added fluoride ion, the above reaction is preferably carried out in the absence of the Brønsted acid. When the Brønsted acid is used in this reaction, it may be the same as those exemplified above.

When the use of the Brønsted acid is preferable, the amount of the acid is at least 0.5 mole per 1 mole of the Brønsted acid salt of diazabicycloalkane of the formula (III). When the acid dissociation constant pKa is 4.6 or less, the amount of the acid is preferably between 0.5 and 2 moles in view of the yield and costs. The amount of the acid is more preferably between 0.5 and 1.5 moles, in particular between 0.8 and 1.2 moles for performing the reaction at high efficiency and high yield.

The above reaction is preferably carried out in the absence of the Brønsted acid, when $(X^1)^-$ in the formula (III) used as the starting material in the above reaction is a conjugated base (HA$^-$) of a dibasic acid ($H_2A$) in the first dissociation state and $(X^1)^-$ and $(X^2)^-$ in the product of the formula (I) together form a conjugated base ($A^{2-}$) of the dibasic acid in the second dissociation state.

The form of fluorine ($F_2$) used in this reaction is the same as that described above. The preferable solvent and reaction temperature employed in this reaction are the same as those described above.

In the third embodiment of the present invention, a N,N'-difluorodiazoniabicycloalkane salt of the formula (I) is prepared by reacting fluorine ($F_2$) and a Brønsted acid salt of a diazabicycloalkane of the formula (IV):

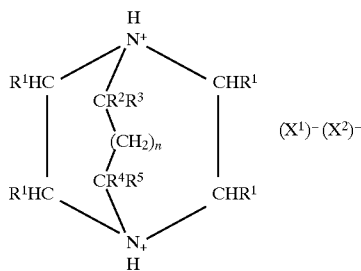

(IV)

wherein $R^1$, $R^2$, $R^3$, $R^4$, $R^5$, n, $(X^1)^-$ and $(X^2)^-$ are the same as defined above, in the presence or absence of a base.

The Brønsted acid salt of a diazabicycloalkane of the formula (IV) used in the above reaction can be easily prepared by mixing the diazabicycloalkane of the formula (II) and at least one of the above described Brønsted acid.

The base used in this reaction may be the diazabicycloalkane of the formula (II) or a base which is conventionally used in organic chemistry. To obtain the desired product in the high yield and efficiency, a base from which a by-product soluble in a solvent is derived in the reaction with the fluorine ($F_2$) is preferably used. Examples of such the base are amines (e.g. ammonia, methylamine, dimethylamine, trimethylamine, ethylamine, diethylamine, triethylamine, benzylamine, benzyltrimethylamine, 1,4-diazabicyclo[2.2.2]octane, etc.); ammonium compounds (e.g. ammonium hydroxide, ammonium carbonate, tetramethylammonium hydroxide, tetrabutylammonium hydroxide, benzyltrimethylammonium hydroxide, tetramethylammonium carbonate, tetraethylammonium carbonate, tetrabutylammonium carbonate, tetramethylammonium fluoride, tetramethylammonium fluoride hydrate, tetraethylammonium fluoride, tetraethylammonium fluoride hydrate, tetrabutylammonium fluoride, terabutylammonium fluoride hydrate, tetramethylammonium formate, teraethylammonium acetate, tetraethylammonium acetate hydrate, tetrabutylammonium acetate, etc.); and the like.

The amount of the base is usually less than 1 mole per 1 mole of the Brønsted acid salt of the diazabicycloalkane of the formula (IV). To obtain the product of high purity, the amount of the base is preferably 0.2 mole or less. More preferably, the amount of the base is 0.1 mole or less in view of the yield and costs.

The form of fluorine ($F_2$) used in this reaction is the same as that described above. The preferable solvent and reaction temperature employed in this reaction are the same as those described above.

An HF addition salt may be formed when at least one of the acid dissociation constants pKa of the dibasic acid in the first and second dissociation states is close to or larger than pKa of hydrogen fluoride (HF), that is, 3.17, in the case where the process of the present invention consists of or comprises the reaction with the fluorine which will be explained below. In this case, to prepare the N,N'-difluorodiazabicycloalkane salt of the formula (I) in which $(X^1)^-$ and $(X^2)^-$ together form a single conjugated base of the Brønsted acid, the HF addition salt is subjected to a treatment for removing HF, for example, heating, vacuum drying, azeotropic boiling, and the like.

In the fourth embodiment of the present invention, a highly pure N,N'-difluorodiazoniabicycloalkane salt of the formula (I) is prepared in a high yield by reacting an acid or salt and a N,N'-difluorodiazoniabicycloalkane salt of the formula (I'):

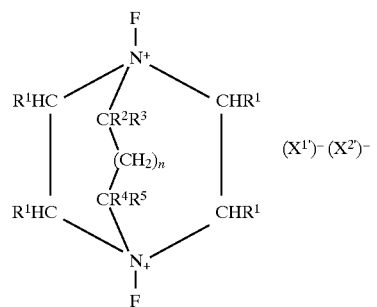

(I')

wherein $(X^{1'})^-$ and $(X2')^-$ represent independently each other a conjugated base of a Brønsted acid or together form a single conjugated base of a Brønsted acid, and $R^1$, $R^2$, $R^3$, $R^4$, $R^5$ and n are the same as defined above, which is obtained in the above described reaction, for inducing a counter anion exchange reaction.

The counter anion exchange reaction is preferably carried out using an acid for producing the highly pure product effectively.

In the above reaction, the acid may be a Brønsted acid or Lewis acid.

The Brønsted may be the same as those described above.

The Lewis acid may be one having substantially the same acidity as that of a Brønsted acid having an acid dissociation constant pKa of about 12.4 or less. The Lewis acid, which reacts with HF and forms a Brønsted acid having an acid dissociation constant of 4.6 or less, in particular, less than 3.17, is preferable. Examples of such the Lewis acid are $BF_3$, $BCl_3$, $BBr_3$, $AsF_3$, $AsF_5$, $PF_3$, $PF_5$, $PCl_5$, $SbF_3$, $SbCl_3$, $SbF_5$, $SbF_3Cl_2$, $SbCl_5$, $AlF_3$, $AlCl_3$, $SiF_4$, $SO_3$, $(CF_3)_3B$, $(C_6H_2F_3)_3B$, $(C_6F_5)_3B$, $NbF_5$, $SeO_3$, $TaF_5$, $TeF_6$, $TiF_4$, $VF_5$, $ZrF_4$, and the like.

The acid used in the above counter ion exchange reaction, that is, the Brønsted acid or Lewis acid may be used in the form of an aqueous solution or a complex with ethers (e.g. diethyl ether, dibutyl ether, dimethyl ether, t-butyl methyl ether, etc.); sulfides (e.g. dimethyl sulfide, diethyl sulfide, etc.); water; alcohols (e.g. methanol, ethanol, propanol, etc.); nitriles (e.g. acetonitrile, propionitrile, etc.); carboxylic acids (e.g. formic acid, acetic acid, etc.); and the like.

As the acid used in the above reaction, the Brønsted acid is preferable for obtaining the product in the high yield.

The salt used in the above reaction may be the salt of the above described Brønsted acid. Preferable salts are metal salts, ammonium salts and phosphonium salts of the above exemplified Brønsted acids. Among them, the metal and ammonium salts are preferable for obtaining the product of high purity at a low cost. In particular, the ammonium salts are preferable since the product is obtained in a high yield effectively.

Preferable examples of the ammonium moiety of the ammonium salt are ammonium, monomethylammonium, dimethylammonium, trimethylammonium, tetramethylammonium, diethylammonium, triethylammonium, tetraethylammonium, tetrabutylammonium, benzyltrimethylammonium, benzyltriethylammonium, (hydroxyethyl)trimethylammonium, (hydroxyethyl)triethylammonium, pyridinium, N-methylpyridinium, quinolinium, and the like, and preferable examples of the metal salts are alkali metal salts and alkaline earth metal salts.

The amount of the acid or salt is selected from a range between 0.75 and 1.3 moles per 1 mole of the compound of the formula (I') when either one of $(X^1)^-$ and $(X^2)^-$ in the formula (I') is exchanged through the counter anion exchange reaction. However, 1.3 moles or more of the acid or salt may be used. In such the case, preferably the amount of the acid or salt does not exceed 10 moles from the economical point of view.

The amount of the acid or salt is preferably at least 1.5 moles per 1 mole of the compound of the formula (I') when both $(X^1)^-$ and $(X^2)^-$ in the formula (I') are exchanged. Preferably, the amount of the acid or salt does not exceed 10 moles from the economical point of view.

When the N,N'-difluorodiazoniabicycloalkane salt of the formula (I) in which $(X^1)^-$ and $(X^2)^-$ together form the single conjugated base of the Brønsted acid is prepared, the amount of the dibasic acid or its salt is preferably in a range between 0.75 and 1.3 moles, more preferably between 0.9 and 1.2 moles per 1 mole of the compound of the formula (I').

The counter anion exchange reaction is carried out in a solvent preferably.

Examples of the solvent are $C_2$–$C_5$ nitriles (e.g. acetonitrile, propionitrile, butyronitrile, isobutyronitrile, valeronitrile, isovaleronitrile, etc.); water; $C_1$–$C_5$ alcohols or halogenated alcohols (e.g. methanol, ethanol, propanol, isopropanol, butanol, isobutanol, sec.-butanol, t-butanol, trifluoroethanol, trichloroethanol, tetrafluoropropanol, pentafluoropropanol, hexafluoroisopropanol, hexafluorobutanol, nonafluoro-t-butanol, octafluoropentanol, nonafluoropentanol, etc.); hydrogen fluoride; $C_1$–$C_4$ alkanoic or haloalkanoic acids (e.g. formic acid, acetic acid, propionic acid, butanoic acid, trifluoroacetic acid, tetrafluoropropionic acid, pentafluoropropionic acid, heptafluorobutanoic acid, etc.); and mixtures thereof.

The reaction temperature is usually selected from a range between about –100° C. and about +80° C. Preferably, the reaction temperature is between –80° C. and +50° C. for performing the reaction at the high yield.

According to the fifth embodiment of the present invention, a N,N'-difluorodiazoniabicycloalkane salt of the formula (I) can be produced in a high yield by reacting the diazabicycloalkane of the formula (II) and the fluorine ($F_2$) in the presence of a Brønsted acid, followed by the reaction with an acid or salt.

The Brønsted acid used in this reaction may be the above exemplified ones. Among them, the oxoacids of sulfur are preferable in view of the yield and costs. In particular, sulfuric acid is preferable because of easy availability.

That is, the N,N'-difluorodiazoniabicycloalkane salt of the formula (I) can be produced with high purity at a high yield by reacting the diazabicycloalkane of the formula (II) and the fluorine ($F_2$) in the presence of the Brønsted acid, preferably sulfuric acid, and then reacting the intermediate product and the acid or salt.

The above process comprises the first step for reacting the diazabicycloalkane of the formula (II) and the fluorine in the presence of the Brønsted acid, and the second step for treating the intermediate product obtained in the first step with the acid or salt. These steps will be explained below by referring to a case where sulfuric acid which is particularly preferable as the Brønsted acid is used.

First step

Sulfuric acid used in this step is readily available as an inexpensive industrial raw material.

The form and amount of the fluorine ($F_2$) used in this step are the same as described above.

The amount of sulfuric acid is preferably at least 0.45 mole, more preferably between 0.45 and 5 moles, in particular between 0.5 and 3 moles per 1 mole of the diazabicycloalkane. Furthermore, the amount of sulfuric acid is desirably between 0.75 and 2.5 moles, more desirably between 0.9 and 2.2 moles in view of the high efficiency and yield.

A solvent is preferably used for performing the reaction in this step. Preferable examples of the solvent are $C_2$–$C_5$ nitriles (e.g. acetonitrile, propionitrile, butyronitrile, isobutyronitrile, valeronitrile, isovaleronitrile, etc.); $C_1$–$C_8$ halohydrocarbons (e.g. methylene chloride, chloroform, carbon tetrachloride, chlorotrifluoromethane, bromotrifluoromethane, dichloroethane, tetrachloroethane, tetrafluoroethane, chlorotrifluoroethane, perfluorobutane, perfluorohexane, perfluorooctane, etc.); water; $C_1$–$C_5$ alcohols or halogenated alcohols (e.g. methanol, ethanol, propanol, isopropanol, butanol, isobutanol, sec.-butanol, t-butanol, trifluoroethanol, trichloroethanol, hexafluoroisopropanol, pentafluoropropanol, tetrafluoropropanol, hexafluorobutanol, nonafluoro-t-butanol, octafluoropentanol, nonafluoropentanol, etc.); hydrogen fluoride; $C_1$–$C_4$ alkanoic or haloalkanoic acids (e.g. formic acid, acetic acid, propionic acid, butanoic acid, trifluoroacetic acid, tetrafluoropropionic acid, pentafluoropropionic acid, heptafluorobutanoic acid, etc.); and mixtures thereof.

Among them, the $C_2$–$C_5$ nitriles, $C_1$–$C_5$ alcohols or halogenated alcohols, $C_1$–$C_4$ alkanoic or haloalkanoic acids or their mixtures are preferable for performing the reaction effectively and obtaining the product in the high yield.

The reaction temperature is usually in the range between about –100° C. and about +80° C. Preferably, the reaction temperature is in the range between –80° C. and +50° C. for performing the reaction in the high yield of the product.

Second step

In this step, the desired N,N'-difluorodiazoniabicycloalkane salt is obtained by reacting the acid or salt with the reaction liquid containing the N,N'-difluorodiazoniabicycloalkane sulfate and/or di(hydrogensulfate) or hydrogensulfate/fluoride, hydrogensulfate/HF-addition fluoride, and the like.

The reaction in the second step comprises the counter anion exchange reaction for the N,N'-difluorodiazoniabicycloalkane salt formed in the first step. The acid is preferably used for the reaction in the second step to produce the product of high purity effectively.

In this reaction, a Brønsted acid or Lewis acid can be used as the acid. The Brønsted acid or Lewis acid may be the same as described above. As in the above described case, the Brønsted acid or Lewis acid may be used in the form of an aqueous solution or in the form of a complex with ethers (e.g. diethyl ether, dimethyl ether, dibutyl ether, t-butyl methyl ether, etc.); sulfides (e.g. dimethyl sulfide, diethyl sulfide, etc.); water; alcohols (e.g. methanol, ethanol, propanol, etc.); nitrites (e.g. acetonitrile, propionitrile, etc.); carboxylic acids (e.g. formic acid, acetic acid, etc.); and the like.

The salt may be the salt of the above described Brønsted acid. Among the salts, the metal and ammonium salts are preferable for obtaining the highly pure product at a low cost. In particular, the ammonium salts are preferable since the product is obtained in the high yield effectively.

Preferable examples of the ammonium moiety of the ammonium salt are ammonium, monomethylammonium, dimethylammonium, trimethylammonium, tetramethylammonium, diethylammonium, triethylammonium, tetraethylammonium, tetrabutylammonium, benzyltrimethylammonium, benzyltriethylammonium, (hydroxyethyl)

trimethylammonium, (hydroxyethyl)triethylammonium, pyridinium, N-methylpyridinium, quinolinium, and the like, and preferable examples of the metal salts are alkali metal salts and alkaline earth metal salts.

The amount of the acid or salt is at least 0.8 mole per 1 mole of the diazabicycloalkane used in the first step, preferably at least 0.9 mole in view of the yield, and more preferably 10 moles or less in view of the costs.

When N,N'-difluorodiazoniabicycloalkane salt of the formula (I) in which $(X^1)^-$ and $(X^2)^-$ are the same (except a case where $(X^1)^-$ and $(X^2)^-$ are the conjugated base of the Brønsted acid used in the first step), the amount of the acid or salt is preferably at least 1.5 moles, more preferably at least 1.7 moles, particularly at least 1.8 moles in view of the yield, and does not exceed 10 moles preferably from the economical point of view.

When the N,N'-difluorodiazoniabicycloalkane salt of the formula (I) in which $(X^1)^-$ and $(X^2)^-$ together form the single conjugated base of the Brønsted acid is prepared, the amount of the dibasic acid or its salt is preferably in a range between 0.75 and 1.3 moles, more preferably between 0.9 and 1.2 moles per 1 mole of the diazabicycloalkane. An HF addition salt may be formed, when the dibasic acid or its salt is used and at least one of the acid dissociation constants pKa of the dibasic acid in the first and second dissociation states is close to or larger than the pKa of hydrogen fluoride (HF), that is, 3.17. Such the HF addition salt is subjected to a treatment for removing HF, for example, heating, vacuum drying, azeotropic boiling, and the like.

The reaction in the second step can be carried out by adding the acid or its salt or a compound containing the acid or salt to the reaction liquid obtained in the first step.

The reaction temperature is usually selected from a range between about −100° C. and about +80° C. Preferably, the reaction temperature is between −80° C. and +50° C. for performing the reaction in view of the yield and reaction efficiency.

For the post treatment of the reaction mixture, the desired product can be isolated by filtration easily, when it is obtained in the form of precipitate.

In the sixth embodiment of the present invention, a N,N'-difluorodiazoniabicycloalkane salt of the formula (I) is also prepared in a high yield by reacting fluorine ($F_2$) and a monoBrønsted acid salt of a diazabicycloalkane of the formula (III'):

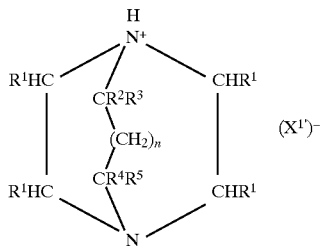

wherein $R^1$, $R^2$, $R^3$, $R^4$, $R^5$, n and $(X^{1'})^-$ are the same as defined above, in the presence or absence of a Brønsted acid, and then reacting the intermediate product and an acid or salt.

This process comprises the step i) for reacting the fluorine and the monoBrønsted acid salt of the diazabicycloalkane of the formula (III') in the presence or absence of a Brønsted acid, and the step ii) for treating the intermediate product obtained in the step i) with an acid or salt. These steps will be explained below in detail.

Step i)

The monoBrønsted acid salt of the diazabicycloalkane of the formula (III') used as the starting material in the step i) is readily prepared by mixing the above diazabicycloalkane of the formula (II) with an equimolar amount of the Brønsted acid.

The Brønsted acid used in this reaction may be the above exemplified ones.

The Brønsted acid may not be used when $(X^{1'})^-$ in the compound of the formula (III') used as the starting material in this step is a conjugated base ($HA^-$) of a dibasic acid in the first dissociation step (described below), while the Brønsted acid may be preferably used in some cases depending on the acidity of the dibasic acid in the second dissociation state.

The Brønsted acid may not be used when $(X^{1'})^-$ in the compound of the formula (III') used as the starting material in this step is a conjugated base ($A^-$) of a monobasic acid (described below), while the Brønsted acid may be preferably used for obtaining the product in the good yield.

When the use of the Brønsted acid is preferable, its amount is preferably at least 0.1 mole per 1 mole of the monoBrønsted acid salt of the diazabicycloalkane of the formula (III') in view of the yield. Furthermore, when the acid dissociation constant pKa is 4.6 or less, the amount of the Brønsted acid is preferably between 0.1 and 2 moles in view of the yield and costs. For effectively performing the reaction at the high yield, the amount of the Brønsted acid is preferably between 0.2 and 1.5 moles, in particular between 0.8 and 1.2 moles.

The form of the fluorine ($F_2$), reaction solvent and reaction temperature in this step are the same as those employed in the above described first step.

Step ii)

In this step, the acid or salt is reacted with the solution containing the N,N'-difluorodiazoniabicycloalkane salt obtained in the step i), and the desired N,N'-difluorodiazoniabicycloalkane salt of the formula (I) is obtained.

The reaction in the step ii) comprises a counter anion exchange reaction for the N,N'-difluorodiazoniabicycloalkane salt. The acid is preferably used for preparing the product of high purity effectively.

The acid used in this reaction may be the above exemplified Brønsted acids or Lewis acids. The acid may be used in the form of a complex with various compounds, or in the form of an aqueous solution as described above.

Examples of the salt are the same as those exemplified in the above described second step.

The amount of the acid or salt, reaction temperature, reaction manner and post-treatment are the same as those in the above second step.

In the seventh embodiment of the present invention, a N,N'-difluorodiazoniabicycloalkane salt of the formula (I) is prepared in a high yield by reacting fluorine ($F_2$) and a Brønsted acid salt of a diazabicycloalkane of the formula (IV'):

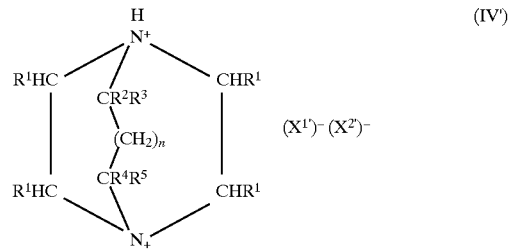

wherein $R^1$, $R^2$, $R^3$, $R^4$, $R^5$, n, $(X^{1'})^-$ and $(X^{2'})^-$ are the same as defined above, in the presence or absence of a base, and then reacting the intermediate product and an acid or salt.

The Brønsted acid salt of the diazabicycloalkane of the formula (IV') is readily prepared by mixing the diazabicycloalkane of the formula (II) and at least one of the above exemplified Brønsted acid. Among them, the oxoacids of sulfur are preferable in view of the yield and costs. In particular, sulfuric acid is preferable because of easy availability.

The above process will be explained by referring to a case where sulfuric acid, which is particularly preferable as the Brønsted acid, is used.

That is, the highly pure N,N'-difluorodiazoniabicycloalkane salt of the formula (I) is prepared in the high yield by reacting the fluorine ($F_2$) with a sulfate salt of a diazabicycloalkane of the formula (V):

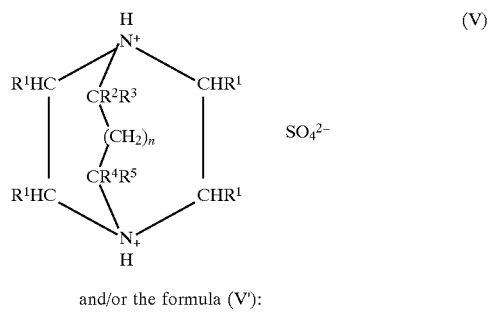

and/or the formula (V'):

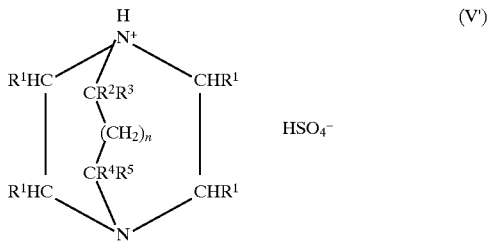

wherein $R^1$, $R^2$, $R^3$, $R^4$, $R^5$ and n are the same as defined above, and/or a di(hydrogensulfate) salt of a diazabicycloalkane of the formula (VI):

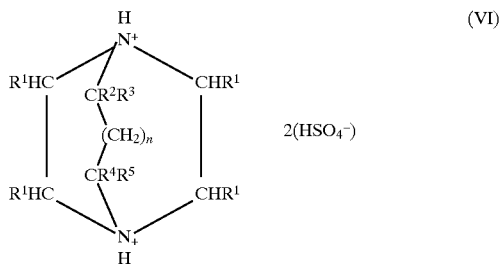

wherein $R^1$, $R^2$, $R^3$, $R^4$, $R^5$ and n are the same as defined above, in the presence or absence of a base, and then reacting the intermediate product and an acid or salt.

This process comprises the step A for reacting the fluorine and the sulfate and/or di(hydrogensulfate) salt of the formulas (V), (V') and (VI) and the step B for treating the reaction product from the step A with the acid or salt. Each step will be explained below.

Step A

The sulfate or di(hydrogensulfate) salt of the formulas (V), (V') or (VI") are readily prepared by reacting 1 or 2 equimolar amounts of sulfuric acid and 1 equimolar amount of the diazabicycloalkane of the formula (II).

The form and amount of the fluorine ($F_2$) and the kind and amount of the base are the same as those explained above. The reaction solvent and reaction temperature preferably used in this step are the same as those employed in the above described first step.

Step B

In the step B, the reaction product obtained in the step A is treated with the acid or salt, and the procedures are the same as those explained in the above second step. The acid is preferably used for preparing the highly pure product effectively. The kind and amount of the acid or salt used in this step and the reaction temperature and the like are the same as those employed in the above second step.

It is apparent that when the diazabicycloalkane of the formula (II) and the Brønsted acid are reacted according to the present invention, the acid readily performs an acid-base reaction with the diazabicycloalkane as a base according to the following reaction schemes and forms various kinds of salts depending on the amount and acidity of the acid.

For example, when the acid is a monobasic Brønsted acid (HA):

Reaction scheme A

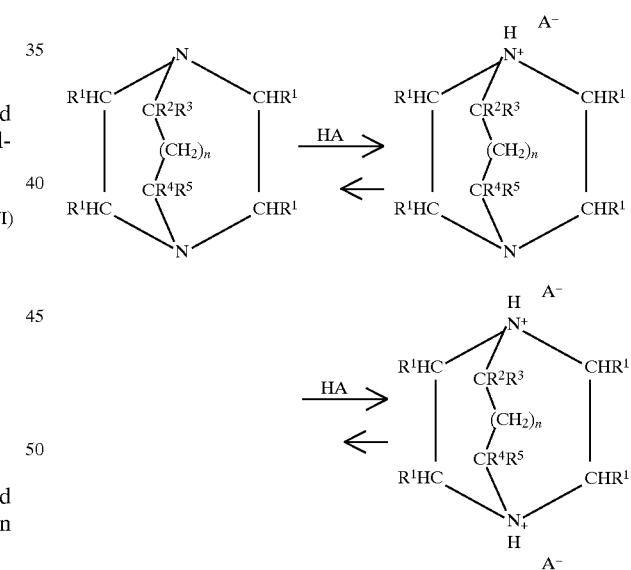

When the acid is a dibasic Brønsted acid ($H_2A$):

Reaction scheme B

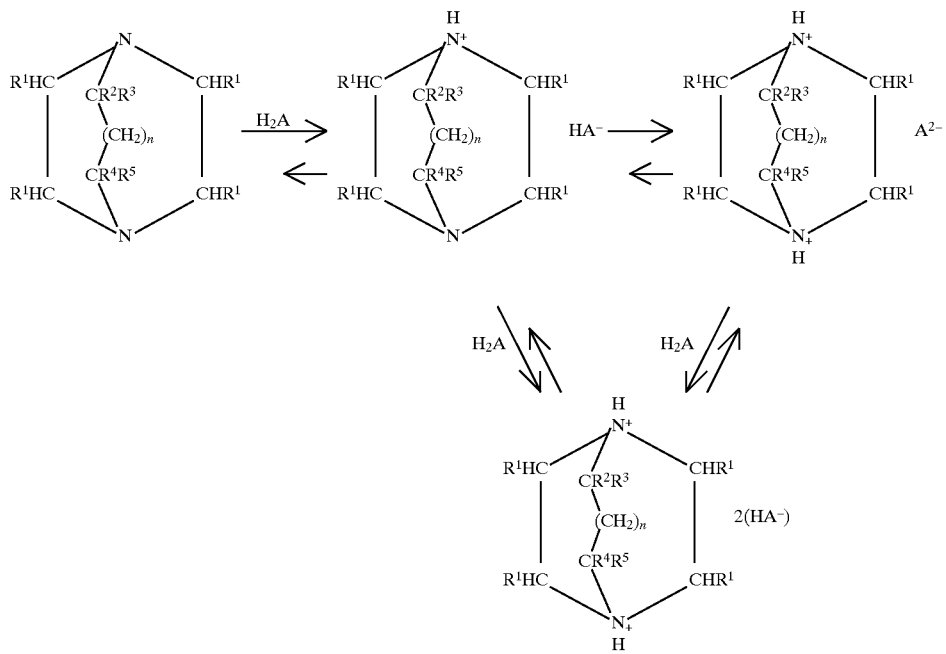

Accordingly, the process using the presynthesized Brønsted acid salt of the diazabicycloalkane of the formula (III), (III'), (IV), (IV') (V), (V') or (VI) corresponds to the process using the specified amount of the acid for the diazabicycloalkane, since the monoBrønsted acid salt of the diazabicycloalkane of the formula (III) or (III'), the Brønsted acid salt of the diazabicycloalkane of the formula (IV) or (IV'), the sulfate salt of the diazabicycloalkane of the formula (V) or (V'), or the di(hydrogensulfate) salt of the diazabicycloalkane of the formula (VI) is one form of these salts.

Furthermore, the use of the Brønsted acid in an amount of less than 2 moles per 1 mole of the diazabicycloalkane of the formula (II) corresponds to the addition of the same diazabicycloalkane to the presynthesized Brønsted acid salt of the diazabicycloalkane of the formula (IV) or (IV'). The use of the Brønsted in an amount exceeding 2 moles corresponds to the addition of the same Brønsted acid to the presynthesized Brønsted acid salt of the diazabicycloalkane of the formula (IV) or (IV').

For example, the addition of 1 mole of the same diazabicycloalkane to the Brønsted acid salt of the diazabicycloalkane of the formula (IV) or (IV') corresponds to the use of 1 mole of the Brønsted acid for 1 mole of the diazabicycloalkane of the formula (II).

The use of 1 mole of the Brønsted acid for 1 mole of the monoBrønsted acid salt of the diazabicycloalkane of the formula (III) or (III') corresponds to the use of 2 moles of the Brønsted acid for 1 mole of the diazabicycloalkane of the formula (II).

The present invention also includes a fluorinating agent comprising the following compounds:

N,N'-Difluoro-1,4-diazoniabicyclo[2.2.0]octane di(hydrogensulfate) of the formula:

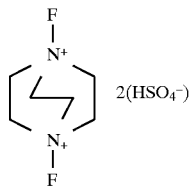

N,N'-difluoro-1,4-diazoniabicyclo[2.2.2]octane salt of the formula:

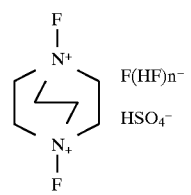

wherein n is a number of 0 to 10, and a method for fluorinating compounds using the fluorinating agent.

The compounds which are fluorinated are organic or inorganic compounds, preferably organic compounds. The organic compounds include any organic compounds such as saturated aliphatic organic compounds, unsaturated aliphatic organic compounds, aromatic organic compounds, condensed aromatic organic compounds, saturated heteroaliphatic organic compounds, unsaturated heteroaliphatic organic compounds, heteroaromatic organic compounds, organometallic compounds, organic polymers, and the like. Among them, nucleophilic organic compounds are preferable.

Among the N,N'-difluorodiazoniabicycloalkane salts of the formula (I), N,N'-difluoro-1,4-diazoniabicyclo[2.2.0] octane di(hydrogensulfate) and N,N'-difluoro-1,4-diazoniabicyclo[2.2.2]octane hydrogensulfate fluoride or its poly(hydrogen fluoride) adduct are particularly useful as useful intermediates or fluorinating agents which are cheap and have high fluorination efficiencies.

EXAMPLES

The present invention will be illustrated by the following examples, which do not limit the scope of the present invention in any way.

Example 1

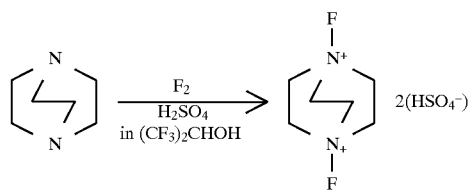

1,1,1,3,3,3-Hexafluoro-2-propanol (40 ml) was added to 1,4-diazabicyclo[2.2.2]octane (10.0 mmol, 1.12 g) in a 200 ml egg plant-type flask. After replacing the internal atmosphere in the flask with argon, the mixture was stirred to form a homogeneous solution. Then, conc. sulfuric acid (19.9 mmol, 1.95 g, 1.1 ml) was added to the solution.

The flask was dipped in a bath kept at −5° C., and diluted fluorine gas ($F_2/N_2$=10/90 (v/v)) was blown in the solution at a flow rate of 40 ml/min. while stirring well. The reaction was terminated after blowing 11,300 ml of the diluted fluorine gas (50.4 mmol of fluorine). After the residual fluorine gas was purged by flowing nitrogen gas, the reaction mixture was allowed to warm up to room temperature.

The crystal precipitated by the addition of diethyl ether (50 ml) was filtrated, and colorless solid N,N'-difluoro-1,4-diazoniabicyclo[2.2.2]octane di(hydrogensulfate) having the purity of 100% (mole %) (3.0 g, 8.72 mmol) was obtained. Yield: 82%.

The properties were shown in Table 1.

Example 2

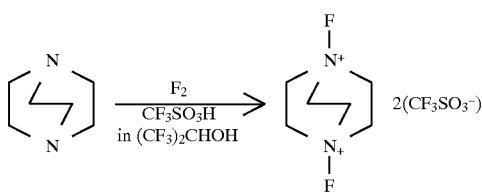

1,1,1,3,3,3-Hexafluoro-2-propanol (40 ml) was added to 1,4-diazabicyclo[2.2.2]octane (20.0 mmol, 2.24 g) in a 100 ml egg plant-type flask. After replacing the internal atmosphere in the flask with argon, the mixture was stirred to form a homogeneous solution. Then, trifluoromethanesulfonic acid (39.0 mmol, 5.85 g) was added to the solution.

The flask was dipped in a bath kept at 0° C., and diluted fluorine gas ($F_2/N_2$=10/90 (v/v)) was blown in the solution at a flow rate of 50 ml/min. while stirring well. The reaction was terminated after blowing 26,880 ml of the diluted fluorine gas (120 mmol of fluorine). After the residual fluorine gas was purged by flowing nitrogen gas, the reaction mixture was allowed to warm up to room temperature.

The solvent was evaporated off from the reaction liquid under reduced pressure, the obtained crystalline solid was recrystallized from acetonitrile, and N,N'-difluoro-1,4-diazoniabicyclo[2.2.2]octane bis(trifluoromethanesulfonate) having the purity of 100% (5.73 g) was obtained. Yield: 64%.

The properties were shown in Table 1.

Example 3

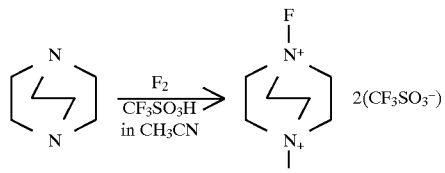

Acetonitrile (12 ml) was added to 1,4-diazabicyclo[2.2.2]octane (3.0 mmol, 337 mg) in a 100 ml egg plant-type flask. After replacing the internal atmosphere in the flask with argon, trifluoromethanesulfonic acid (5.85 mmol, 878 mg) was added to the mixture.

The flask was dipped in a bath kept at −30° C., and diluted fluorine gas ($F_2/N_2$=10/90 (v/v)) was blown in the solution at a flow rate of 30 ml/min. while stirring well. The reaction was terminated after blowing 4023 ml of the diluted fluorine gas (18 mmol of fluorine). After the residual fluorine gas was purged by flowing nitrogen gas, the reaction mixture was allowed to warm up to room temperature.

The solvent was evaporated off from the reaction liquid under reduced pressure. The residual solid was thoroughly washed with diethyl ether, and N,N'-difluoro-1,4-diazoniabicyclo[2.2.2]octane bis(trifluoromethanesulfonate) (1.13 g, yield: 84%) was obtained.

This product was analyzed by $^1$H- and $^{19}$F-NMR. The purity of N,N'-difluoro-1,4-diazoniabicyclo[2.2.2]octane bis(trifluoromethanesulfonate) was 95%, and 5% of N,N-dihydro-1,4-diazoniabicyclo[2.2.2]octane bis(trifluoromethanesulfonate) was contained as the impurity.

After adding trifluoromethanesulfonic acid (45 mg, 0.3 mmol) was added to the above product (1.13 g), the product was recrystallized from acetonitrile, and N,N'-difluoro-1,4-diazoniabicyclo[2.2.2]octane bis(trifluoromethanesulfonate) having the purity of 100% (0.834 g) was obtained. Yield: 62%.

The properties were shown in Table 1.

Example 4

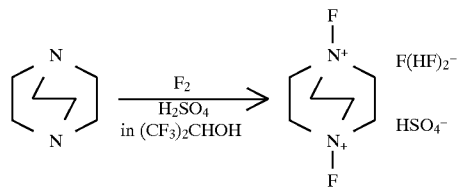

1,1,1,3,3,3-hexafluoro-2-propanol (12 ml) and sulfuric acid (3.0 mmol, 0.249 g) were added to 1,4-diazabicyclo[2.2.2]octane (3.0 mmol, 337 mg) in a 50 ml egg plant-type flask.

The flask was dipped in a bath kept at −5° C., and diluted fluorine gas ($F_2/N_2$=10/90 (v/v)) was blown in the reaction liquid at a flow rate of 30 ml/min. while stirring well. The reaction was terminated after blowing 4032 ml of the diluted fluorine gas (18 mmol of fluorine). After the residual fluorine gas was purged by flowing nitrogen gas, the reaction mixture was allowed to warm up to room temperature.

The reaction liquid was concentrated under reduced pressure. After adding methylene chloride, the formed crystal was filtrated. The obtained crystal was thoroughly washed with methylene chloride, and colorless solid N,N'-difluoro-1,4-diazoniabicyclo[2.2.2]octane hydrogensulfate di(hydrogen fluoride) fluoride having the purity of 100% (0.588 g) was obtained. Yield: 61%.

The properties were shown in Table 1.

Example 5

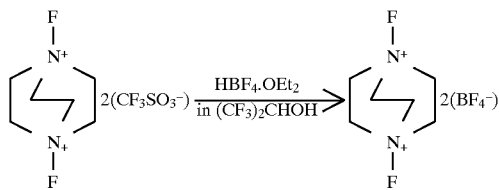

N,N'-Difluoro-1,4-diazoniabicyclo[2.2.2]octane bis(trifluoromethanesulfonate) (8.0 mmol, 3.61 g) was charged in a 100 ml round flask. After replacing the internal atmosphere in the flask with argon, 1,1,1,3,3,3-hexafluoro-2-propanol (36 ml) was added while stirring to form a homogeneous solution. Then, a tetrafluoroboric acid-diethyl ether complex (20 mmol, 3.24 g) was dropwise added to the solution at room temperature, followed by stirring for one hour. The precipitated crystal was filtrated.

The collected crystal was thoroughly washed with methylene chloride, and colorless solid N,N'-difluoro-1,4-diazoniabicyclo[2.2.2]octane bis(tetrafluoroborate) having the purity of 100% (7.24 mmol, 2.34 g) was obtained. Yield: 90%.

The properties were shown in Table 2.

Example 6

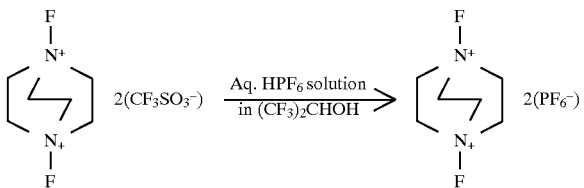

N,N'-Difluoro-1,4-diazoniabicyclo[2.2.2]octane bis(trifluoromethanesulfonate) (1.19 mmol, 0.535 g) was charged in a 30 ml round flask. After replacing the internal atmosphere in the flask with argon, 1,1,1,3,3,3-hexafluoro-2-propanol (5 ml) was added while stirring to form a homogeneous solution. Then, a 60% aqueous solution of hexafluorophosphoric acid (2.6 mmol, 0.385 g) was dropwise added to the solution at room temperature, followed by stirring for 15 minutes.

The precipitated crystal was thoroughly washed with diethyl ether, and colorless solid N,N'-difluoro-1,4-diazoniabicyclo[2.2.2]octane bis(hexafluorophosphate) having the purity of 100% (0.348 g) was obtained.

Diethyl ether was added to the filtrate. The precipitated crystal was filtrated and thoroughly washed with diethyl ether, and N,N'-difluoro-1,4-diazoniabicyclo[2.2.2]octane bis(hexafluorophosphate) having the purity of 100% (0.093 g) was obtained. Total yielded amount: 0.441 g (total yield: 85%).

The properties were shown in Table 2.

Example 7

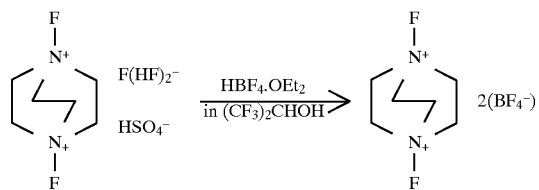

N,N'-Difluoro-1,4-diazoniabicyclo[2.2.2]octane hydrogensulfate dihydrogen fluoride fluoride (0.246 g, 0.81 mmol) was charged in a 10 ml egg plant-type flask, and 1,1,1,3,3,3-hexafluoro-2-propanol (4 ml) was added. Then, a tetrafluoroboric acid-diethyl ether complex (0.356 g, 2.2 mmol) was dropwise added at room temperature, followed by stirring for one hour at room temperature. The precipitated crystal was filtrated.

The obtained crystal was thoroughly washed with diethyl ether, and colorless solid N,N'-difluoro-1,4-diazoniabicyclo[2.2.2]octane bis(tetrafluoroborate) having the purity of 100% (0.262 9) was obtained. Yield: 100%.

The properties were shown in Table 2.

Example 8

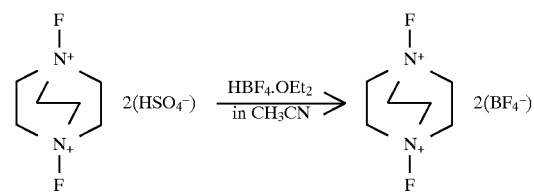

A tetrafluoroboric acid-diethyl ether complex (0.679 g, 4.2 mmol) was dropwise added to a suspension of N,N'-difluoro-1,4-diazoniabicyclo[2.2.2]octane di(hydrogensulfate) (0.669 g, 2.0 mmol) in acetonitrile (4 ml) which was well stirred at room temperature, followed by stirring for further 15 minutes at room temperature. The precipitated crystal was filtrated and washed with ether, followed by drying under reduced pressure, and N,N'-difluoro-1,4-diazoniabicyclo[2.2.2]octane bis(tetrafluoroborate) having the purity of 100% (0.530 g) was obtained. Yield: 82%.

The properties were shown in Table 2.

Example 9

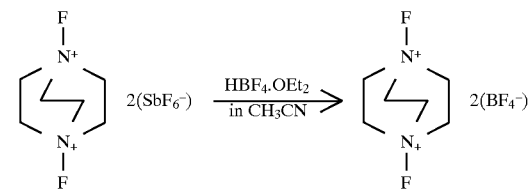

A tetrafluoroboric acid-diethyl ether complex (0.706 g, 4.37 mmol) was dropwise added to a suspension of N,N'-difluoro-1,4-diazoniabicyclo[2.2.2]octane bis(hexafluoroantimonate) (1.29 g, 2.08 mmol) in acetonitrile (8 ml) which was well stirred at room temperature, followed by stirring for further 15 minutes at room temperature. The precipitated crystal was filtrated and washed with ether, followed by drying under reduced pressure, and N,N'-difluoro-1,4-diazoniabicyclo[2.2.2]octane bis (tetrafluoroborate) having the purity of 100% (0.650 g) was obtained. Yield: 97%.

The properties were shown in Table 2.

Example 10

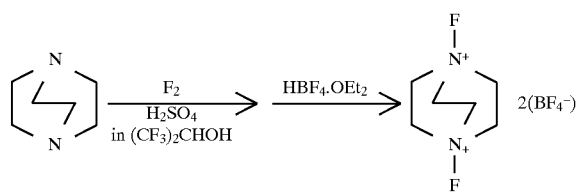

1,1,1,3,3,3-Hexafluoro-2-propanol (60 ml) was added to 1,4-diazabicyclo[2.2.2]octane (15.0 mmol, 1.68 g) in a 200 ml egg plant-type flask. After replacing the internal atmosphere in the flask with argon, the mixture was stirred to form a homogeneous solution. Then, conc. sulfuric acid (15.0 mmol, 1.47 9) was added to the solution.

The flask was dipped in a bath kept at −5° C., and diluted fluorine gas ($F_2/N_2$=10/90 (v/v)) was blown in the solution at a flow rate of 40 ml/min. The diluted fluorine gas of 20,160 ml (90 mmol of fluorine) was blown. Then, the residual fluorine gas was purged by flowing nitrogen gas.

After allowing the reaction mixture to warm up to room temperature, a tetrafluoroboric acid-diethyl ether complex (33 mmol, 5.34 g) was dropwise added, followed by stirring for 30 minutes. The precipitated crystal was filtrated and washed with diethyl ether, and colorless solid N,N'-difluoro-1,4-diazoniabicyclo[2.2.2]octane bis(tetrafluoroborate) having the purity of 100% (11.6 mmol, 3.76 g) was obtained. Yield: 77%.

The properties were shown in Table 2.

Example 11

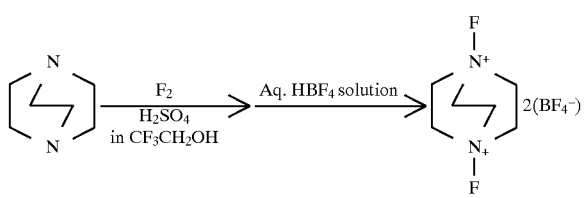

2,2,2-Trifluoroethanol (12 ml) was added to 1,4-diazabicyclo[2.2.2]octane (3.0 mmol, 337 mg) in a 50 ml egg plant-type flask. After replacing the internal atmosphere in the flask with argon, conc. sulfuric acid (3.0 mmol, 249 mg) was added to the solution while stirring.

The flask was dipped in a bath kept at −5° C., and diluted fluorine gas ($F_2/N_2$=10/90 (v/v)) was blown in the solution at a flow rate of 30 ml/min. The diluted fluorine gas of 5136 ml (23 mmol of fluorine) was blown. Then, the residual fluorine gas was purged by flowing nitrogen gas.

After allowing the reaction mixture to warm up to room temperature, a 42% aqueous solution of tetrafluoroboric acid (1.38 g, 6.6 mmol of tetrafluoroboric acid) was dropwise added while stirring, and additional 2,2,2-trifluoroethanol (30 ml) was added, followed by stirring for 13 hours at room temperature. The precipitated crystal was filtrated and thoroughly washed with diethyl ether, and colorless solid N,N'-difluoro-1,4-diazoniabicyclo[2.2.2]octane bis (tetrafluoroborate) having the purity of 100% (608 mg, 1.88 mmol) was obtained. Yield: 63%.

The properties were shown in Table 2.

Example 12

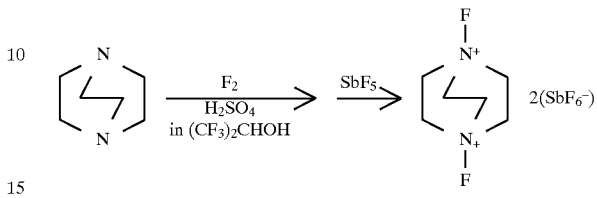

1,1,1,3,3,3-Hexafluoro-2-propanol (12 ml) was added to 1,4-diazabicyclo[2.2.2]octane (3.0 mmol, 337 mg) in a 50 ml egg plant-type flask. After replacing the internal atmosphere in the flask with argon, conc. sulfuric acid (3.0 mmol, 249 mg) was added to the solution while stirring.

The flask was dipped in a bath kept at −5° C., and diluted fluorine gas ($F_2/N_2$=10/90 (v/v)) was blown in the solution at a flow rate of 30 ml/min. The diluted fluorine gas of 4032 ml (18 mmol of fluorine) was blown. Then, the residual fluorine gas was purged by flowing nitrogen gas.

After allowing the reaction mixture to warm up to room temperature, a solution of antimony pentafluoride (6.6 mmol, 1.43 g) in 1,1,1,3,3,3-hexafluoro-2-propanol (10 ml) was dropwise added, followed by stirring for 45 minutes. The precipitated crystal was filtrated and thoroughly washed with methylene chloride and colorless solid N,N'-difluoro-1,4-diazoniabicyclo[2.2.2]octane bis(hexafluoroantimonate) having the purity of 100% (2.60 mmol, 1.62 g) was obtained. Yield: 87%.

The properties are shown in Table 2.

Example 13

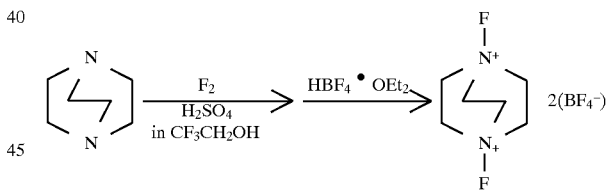

2,2,2-Trifluoroethanol (12 ml) was added to 1,4-diazabicyclo[2.2.2]octane (3.0 mmol, 0.337 g) in a 100 ml egg plant-type flask. After replacing the internal atmosphere in the flask with argon, the mixture was stirred to form a homogeneous solution. Then, conc. sulfuric acid (3.0 mmol, 0.249 g) was added to the solution.

The flask was dipped in a bath kept at −30° C., and diluted fluorine gas ($F_2/N_2$=10/90 (v/v)) was blown in the solution at a flow rate of 30 ml/min. while stirring well. The fluorine gas of 4023 ml (18 mmol of fluorine) was blown. Then, the residual fluorine gas was purged by flowing nitrogen gas.

After allowing the reaction mixture to warm up to room temperature, a tetrafluoroboric acid-diethyl ether complex (6.6 mmol, 1.07 g) was dropwise added, followed by stirring for one hour. The precipitated crystal was filtrated and thoroughly washed with diethyl ether, and colorless solid N,N'-difluoro-1,4-diazoniabicyclo[2.2.2]octane bis (tetrafluoroborate) having the purity of 100% (0.804 g) was obtained. Yield: 83%.

The properties were shown in Table 2.

Example 14

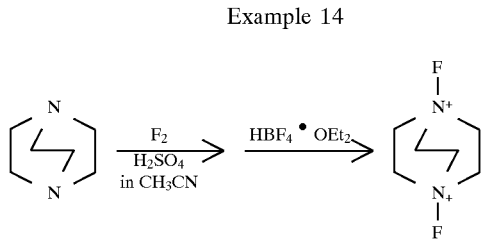

Acetonitrile (12 ml) was added to 1,4-diazabicyclo[2.2.2]octane (3.0 mmol, 0.337 g) in a 100 ml egg plant-type flask. After replacing the internal atmosphere in the flask with argon, the mixture was stirred to form a homogeneous solution. Then, conc. sulfuric acid (3.0 mmol, 0.294 g) was added to the solution.

The flask was dipped in a bath kept at −30° C., and diluted fluorine gas ($F_2/N_2$=10/90 (v/v)) was blown in the solution at a flow rate of 30 ml/min. while stirring well. The fluorine gas of 4635 ml (20.7 mmol of fluorine) was blown. Then, the residual fluorine gas was purged by flowing nitrogen gas.

After allowing the reaction mixture to warm up to room temperature, a tetrafluoroboric acid-diethyl ether complex (6.6 mmol, 1.07 g) was dropwise added, followed by stirring for one hour. The crystal, which was precipitated by the addition of diethyl ether, was filtrated and thoroughly washed with diethyl ether, and colorless solid N,N'-difluoro-1,4-diazoniabicyclo[2.2.2]octane bis(tetrafluoroborate) having the purity of 100% (0.621 g) was obtained. Yield: 64%.

The properties were shown in Table 2.

Example 15

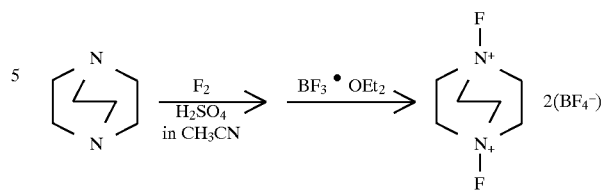

Acetonitrile (12 ml) was added to 1,4-diazabicyclo[2.2.2]octane (0.337 mg, 3.0 mmol) in a 100 ml egg plant-type flask. After replacing the internal atmosphere in the flask with argon, conc. sulfuric acid (0.294 g, 3.0 mmol) was dropwise added to the solution at room temperature.

The flask was dipped in a bath kept at −30° C., and diluted fluorine gas ($F_2/N_2$=10/90 (v/v)) was blown in the solution at a flow rate of 30 ml/min. while stirring well. The reaction was terminated after 4032 ml of the diluted fluorine gas (18.0 mmol of fluorine) was blown. Then, the residual fluorine gas was purged by flowing nitrogen gas.

After that, a boron trifluoride-diethyl ether complex (0.937 g, 6.6 mmol) was dropwise added to the reaction solution. Then, the reaction mixture was allowed to warm up to room temperature, followed by stirring for additional 10 minutes. The precipitated crystal was filtrated and thoroughly washed with methylene chloride and colorless solid N,N'-difluoro-1,4-diazoniabicyclo[2.2.2]octane bis(tetrafluoroborate) having the purity of 100% (0.695 g) was obtained. Yield: 72%.

The properties were shown in Table 2.

TABLE 1

Properties of N,N'-difluorodiazoniabicycloalkane salts

| Ex. No. | Decomposition temp. | $^1$H-NMR (ppm, TMS, int. standard) | $^{19}$F-NMR (ppm, CFCl$_3$, int. standard) | IR (cm$^{-1}$, nujol) | Elemental analysis | | | | | | | | | |
|---|---|---|---|---|---|---|---|---|---|---|---|---|---|---|
| | | | | | Found (%) | | | | | Calculated (%) | | | | |
| | | | | | C | H | N | F | S | C | H | N | F | S |
| 1 | 80° C. | 4.64 (br, s) in D$_2$SO$_4$ | 42.6 (br, s) in D$_2$SO$_4$ | 3048, 1266, 1168, 1019, 854 | 20.75 | 4.50 | 7.94 | — | — | 20.93 | 4.10 | 8.14 | — | — |
| 2, 3, 26 | about 170° C.* | 5.07 (dd, J = 3.5, 3.5 Hz) in CD$_3$CN | 39.2 (2F, br, s, 2xNF) −78.1 (6F, s, 2xCF$_3$) in CD$_3$CN | 3039, 1262, 1169, 1037, 867 | 21.42 | 2.77 | 6.04 | — | — | 21.43 | 2.70 | 6.25 | — | — |
| 4 | 100° C. | 4.64 (br, s) in D$_2$SO$_4$ | 39.8 (br, s) −127 (v.br. peak) in DCOOD | 3051, 1270, 1228, 1045, 874 | 21.49 | 4.64 | 8.12 | 27.9 | 8.5 | 21.30 | 4.47 | 8.28 | 28.1 | 9.5 |

Note: *Starting temperature of the decomposition measured by a differential scanning calorimeter (at a heating rate of 10° C./min.)

TABLE 2

Properties of N,N'-difluorodiazoniabicycloalkane salts

| Ex. No. | Decomposition temp. | $^1$H-NMR (ppm, TMS, int. standard) | $^{19}$F-NMR (ppm, CFCl$_3$, int. standard) | IR (cm$^{-1}$, nujol) | Elemental analysis Found (%) | | | Calculated (%) | | |
|---|---|---|---|---|---|---|---|---|---|---|
| | | | | | C | H | N | C | H | N |
| 5, 7–11, 13–15, 25 | about 170° C.* | 5.02 (dd, J=3.5, 3.5 Hz) in CD$_3$CN | 39.2 (2F, br.s, 2xNF) −150.2 (8F, s, 2xBF$_4$) in CD$_3$CN | 3072, 1062, 851 | 22.35 | 3.61 | 8.39 | 22.26 | 3.74 | 8.65 |
| 6, 23 | about 155° C.* | 4.95 (dd, J=3.5, 3.5 Hz) in CD$_3$CN | 38.9 (2F, br.s, 2xNF) −69.5 (12F, d, J=352 Hz, 2xPF$_6$) in CD$_3$CN | 3073, 1103, 861, 831, 559 | 16.58 | 2.76 | 6.41 | 16.38 | 2.75 | 6.37 |
| 12 | about 200° C. | 4.96 (dd, J=3.5, 3.5 Hz) in CD$_3$CN | 38.9 (2F, br.s, 2xNF) −96.5 to −150.0 (12F, br.m, 2xSbF$_6$) in CD$_3$CN | 3067, 1102, 853, 662, 635 | 11.76 | 1.86 | 4.43 | 11.59 | 1.95 | 4.51 |

Note: *Starting temperature of the decomposition measured by a differential scanning calorimeter (at a heating rate of 10° C./min.)

Examples 16–22

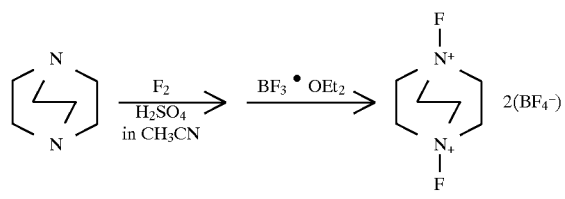

As understood from Table 3, completely or substantially pure N,N'-difluoro-1,4-diazoniabicyclo[2.2.2]octane bis(tetrafluoroborate) was obtained in the high yield.

When the purity was less than 100% in Table 3, the impurity was N,N'-dihydro-1,4-diazoniabicyclo[2.2.2]octane bis(tetrafluoroborate).

TABLE 3

F—$^+$N〈 〉N$^+$—F 2(BF$_4^-$)

| Ex. No. | Amount of N〈 〉N | Amount of H$_2$SO$_4$ | Amount of BF$_3$.OEt$_2$ | Molar ratio N/H$_2$SO$_4$ | Yield | Purity |
|---|---|---|---|---|---|---|
| 16 | 3 mmol | 3.06 mmol | 6.48 mmol | 1/1.02 | 62% | 100% |
| 17 | 3 mmol | 3.12 mmol | 6.51 mmol | 1/1.04 | 65% | 100% |
| 18 | 3 mmol | 3.39 mmol | 6.33 mmol | 1/1.13 | 77% | 98.2% |
| 19 | 3 mmol | 3.93 mmol | 6.36 mmol | 1/1.31 | 83% | >99.8% |
| 20 | 3 mmol | 4.5 mmol | 6.36 mmol | 1/1.5 | 88% | 100% |
| 21 | 3 mmol | 5.13 mmol | 6.36 mmol | 1/1.71 | 87% | 99.6% |
| 22 | 3 mmol | 6.00 mmol | 6.36 mmol | 1/2.00 | 81% | 97.2% |

A reaction and post-treatment were carried out in the same manner as in Example 15 except that raw materials shown in Table 3 in amounts of Table 3 were reacted with dilute fluorine gas at −20° C., and the obtained crystal was washed with methylene chloride and diethyl ether. The results are also shown in Table 3.

Example 23

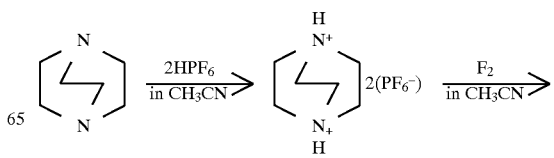

-continued

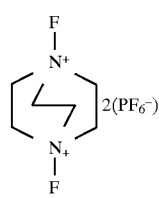

1,4-Diazabicyclo[2.2.2]octane (45.1 mmol, 5.06 g) was charged in a 100 ml round flask made of POLYFLON (trademark, polytetrafluoroethylene manufactured by DAIKIN INDUSTRIES, LTD.). After replacing the internal atmosphere in the flask with argon, acetonitrile (50 ml) was added.

After cooling the solution to 0° C., a 60% aqueous solution of hexafluorophosphoric acid ($HPF_6$) (94.7 mmol) was added to the solution while stirring, followed by evaporating off the solvent at room temperature under reduced pressure. The obtained solid was thoroughly washed with diethyl ether and then dried, and N,N'-dihydro-1,4-diazoniabicyclo[2.2.2]octane bis(hexafluorophosphate) was obtained quantitatively.

N,N'-Dihydro-1,4-diazoniabicyclo[2.2.2]octane bis (hexafluorophosphate) (3.0 mmol, 1.21 g) was charged in a separate 100 ml round flask made of POLYFLON. After replacing the internal atmosphere in the flask with argon, acetonitrile (12 ml) was added and stirred to form a solution. Then, the flask was dipped in a bath kept at −30° C., and diluted fluorine gas ($F_2/N_2$=10/90 (v/v)) was blown in the solution at a flow rate of 30 ml/min. while stirring well. The diluted fluorine gas of 4032 ml (18 mmol of fluorine) was blown. Then, the residual fluorine gas was purged by flowing nitrogen gas.

After allowing the reaction mixture to warm up to room temperature, insoluble materials were filtrated off. The solvent was evaporated off from the filtrate, followed by drying under reduced pressure, and colorless crystalline N,N'-difluoro-1,4-diazoniabicyclo[2.2.2]octane bis (hexafluorophosphate) having the purity of 100% (1.07 g) was obtained. Yield: 81%.

The properties were shown in Table 2.

Example 24

Anisole was fluorinated with N,N'-difluoro-1,4-diazoniabicyclo[2.2.2]octane di(hydrogensulfate) according to the present invention as a fluorinating agent under the reaction condition shown in Table 4. The results are also shown in Table 4.

As seen from Example 24, the fluorination proceeds smoothly under the condition of room temperature and the reaction time of 15 minutes in formic acid, and fluoroanisoles are formed in the good yields, when N,N'-difluoro-1,4-diazoniabicyclo[2.2.2]octane salt comprising the hydrogensulfate ion ($HSO_4^-$), which has a proton for activating the fluorination reaction as a counter anion, is used. Accordingly, the N,N'-difluoro-1,4-diazoniabicyclo[2.2.2] octane di(hydrogensulfate), and hydrogensulfate fluoride or its poly(hydrogen fluoride) which have the activation ability by themselves are expected to achieve the high fluorination efficiency in the fluorination carried out in a neutral organic solvent, and therefore they seem to be promising fluorinating agents having a wide variety of applications.

TABLE 4

| Fluorinating agent | Anisole | Solvent | Reaction time | Reaction temp. | Conversion of anisole (%) | o-Fluoro-anisole | p-Fluoro-anisole | 2,4-Difluoro-anisole | Total |
|---|---|---|---|---|---|---|---|---|---|
| Example 24 (N,N'-difluoro-1,4-diazoniabicyclo[2.2.2]octane 2($HSO_4^-$)) 1 mmol | 1 mmol | HCOOH 2 ml | 15 min. | Room temp. | 92 | 33 | 29 | 4 | 66 |

Example 25

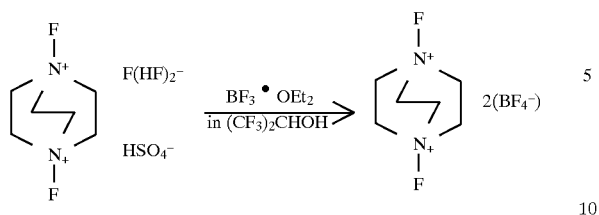

A boron trifluoride-diethyl ether complex (1.55 g, 10.9 mmol) was added to a solution of N,N'-difluoro-1,4-diazoniabicyclo[2.2.2]octane hydrogensulfate di(hydrogen fluoride) fluoride (1.76 g, 5.2 mmol) in 1,1,1,3,3,3-hexafluoro-2-propanol (5 ml) in a nitrogen atmosphere at room temperature. After stirring the solution at room temperature for 15 minutes, the solid was filtrated and washed with 1,1,1,3,3,3-hexafluoro-2-propanol, dichloromethane and then diethyl ether (each one time), followed by drying under reduced pressure, and crystalline N,N'-difluoro-1,4-diazoniabicyclo[2.2.2]octane bis(tetrafluoroborate) having the purity of 100% (1.10 g) was obtained. Yield: 66%.

The properties are shown in Table 2.

Example 26

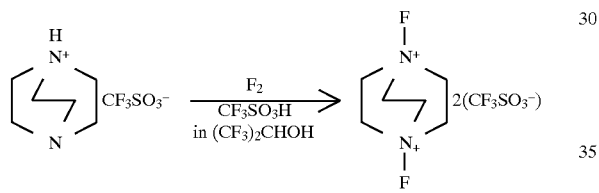

1,1,1,3,3,3-hexafluoro-2-propanol (12 ml) was added to 1,4-diabicyclo[2.2.2]octane monotrifluoromethanesulfonate salt (3.0 mmol, 0.787 g) in a 100 ml egg plant-type flask. After replacing the internal atmosphere in the flask with argon, the mixture was stirred to form a homogeneous solution, and trifluoromethane-sulfonic acid (2.85 mmol, 0.428 g) was added to the solution.

The flask was dipped in a bath kept at 0° C., and diluted fluorine gas ($F_2/N_2$=10/90 (v/v)) was blown in the solution at a flow rate of 30 ml/min. while stirring well. The reaction was terminated after 4032 ml of the diluted fluorine gas (18.0 mmol of fluorine) was blown. Then, the residual fluorine gas was purged by flowing nitrogen gas.

After allowing the reaction mixture to warm up to room temperature, the solvent was evaporated off from the reaction liquid under reduced pressure, and the desired product having the purity of 98% (1.45 g) was obtained (quantitative yield). This crystalline solid was recrystallized from acetonitrile, and N,N'-difluoro-1,4-diazoniabicyclo[2.2.2]octane bis(trifluoromethane-sulfonate) having the purity of 100% (0.816 g) was obtained. Yield: 61%.

The properties were shown in Table 1.

What is claimed is:

1. A process for preparing a N,N'-difluorodiazoniabicycloalkane salt of the formula (I):

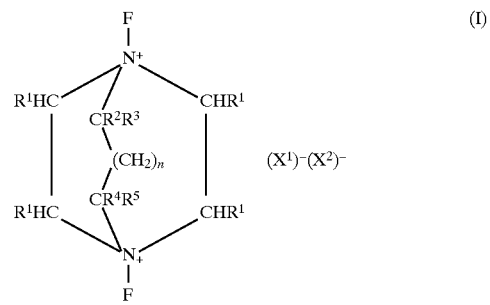

wherein $R^1$, $R^2$, $R^3$, $R^4$ and $R^5$ represent independently of each other a hydrogen atom, a $C_1$–$C_6$ alkyl group, an aryl group, a $C_1$–$C_6$ alkyl group-substituted aryl group or an aryl group-substituted $C_1$–$C_6$ alkyl group, $(X^1)^-$ and $(X^2)^-$ represent independently of each other a conjugated base of a Brønsted acid or together form a single conjugated base of a Brønsted acid, and n is 0, 1 or 2, comprising the step of reacting fluorine and a diazabicycloalkane of the formula (II):

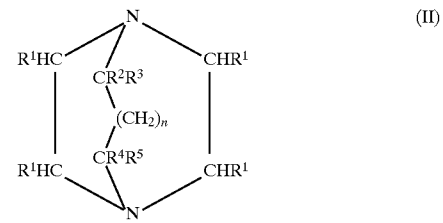

wherein $R^1$, $R^2$, $R^3$, $R^4$, $R^5$ and n are the same as defined above in the presence of a Brønsted acid.

2. The process for preparing a N,N'-difluorodiazoniabicycloalkane salt of the formula (I):

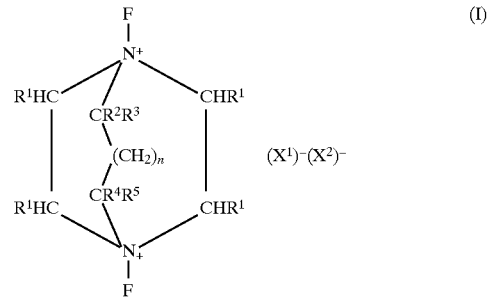

wherein $R^1$, $R^2$, $R^3$, $R^4$, $R^5$, n, $(X^1)^-$ and $(X^2)^-$ are the same as defined in claim 1, comprising the step of reacting fluorine and a monoBrønsted acid salt of a diazabicycloalkane of the formula (III):

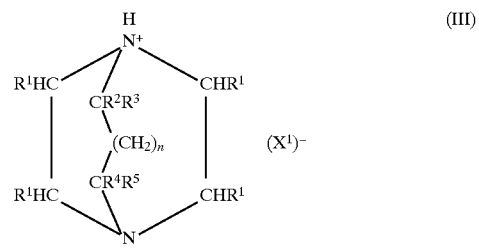

wherein $R^1$, $R^2$, $R^3$, $R^4$, $R^5$, n and $(X^1)^-$ are the same as defined above, in the presence or absence of a Brønsted acid.

3. The process for preparing a N,N'-difluorodiazoniabicycloalkane salt of the formula (I):

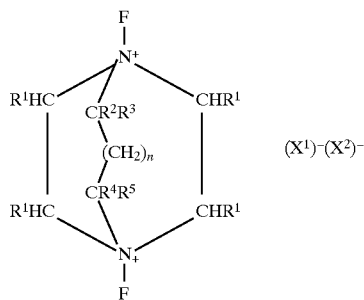

wherein $R^1$, $R^2$, $R^3$, $R^4$, $R^5$, n, $(X^1)^-$ and $(X^2)^-$ are the same as defined in claim 1, comprising the step of reacting fluorine and a Brønsted acid salt of a diazabicycloalkane of the formula (IV):

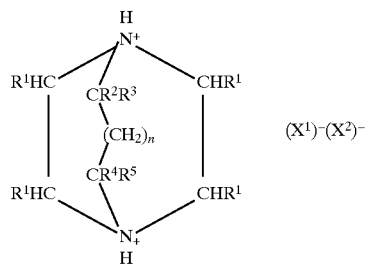

wherein $R^1$, $R^2$, $R^3$, $R^4$, $R^5$, n, $(X^1)^-$ and $(X^2)^-$ are the same as defined in claim 1, in the presence or absence of a base.

4. The process for preparing a N,N'-difluorodiazoniabicycloalkane salt of the formula (I):

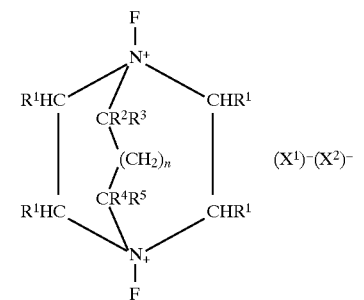

wherein $R^1$, $R^2$, $R^3$, $R^4$, $R^5$, n, $(X^1)^-$ and $(X^2)^-$ are the same as defined in claim 1, comprising the step of reacting an acid or salt and a N,N'-difluorodiazoniabicycloalkane salt of the formula (I'):

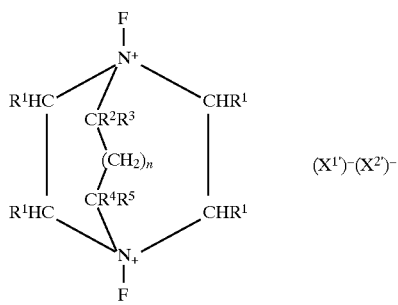

wherein $(X^{1'})^-$ and $(X^{2'})^-$ represent independently of each other a conjugated base of a Bronsted acid or together form a single conjugated base of a Bronsted acid wherein at least one of $(X^1)^-$ and $(X^2)^-$ is different from at least one of $(X^{1'})^-$ and $(X^{2'})^-$, wherein a combination of $(X^1)^-$ and $(X^2)^-$ is different from a combination of $(X^{1'})^-$ and $(X^{2'})^-$, and $R^1$, $R^2$, $R^3$, $R^4$, $R^5$ and n are the same as defined in claim 1.

5. N,N'-difluoro-1,4-diazoniabicyclo[2.2.2]octane salt of the formula:

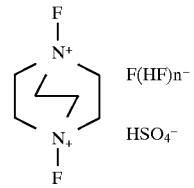

wherein n is a number of 0 to 10.

6. The process for preparing a N,N'-difluorodiazoniabicycloalkane salt of the formula (I):

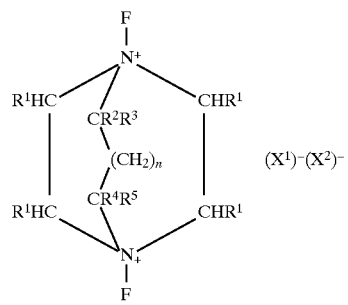

wherein $R^1$, $R^2$, $R^3$, $R^4$, $R^5$, n, $(X^1)^-$ and $(X^2)^-$ are the same as defined in claim 1, comprising the steps of reacting fluorine and a diazabicycloalkane of the formula (II):

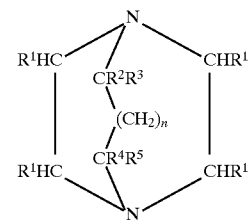

wherein $R^1$, $R^2$, $R^3$, $R^4$, $R^5$ and n are the same as defined in claim 1, in the presence of a Brønsted acid, and then reacting the intermediate product with an acid or salt.

7. A process for preparing a N,N'-difluorodiazoniabicycloalkane salt of the formula (I):

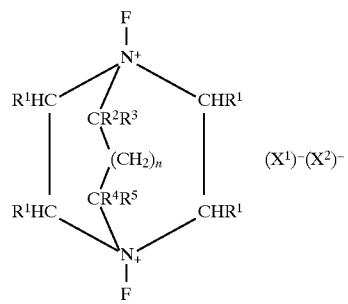

wherein $R^1$, $R^2$, $R^3$, $R^4$, $R^5$, n, $(X^1)^-$ and $(X^2)^-$ are the same as defined in claim 1, comprising the steps of reacting fluorine and a diazabicycloalkane of the formula (II):

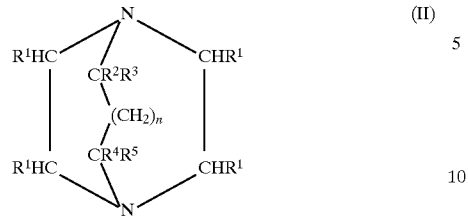

wherein $R^1$, $R^2$, $R^3$, $R^4$, $R^5$ and n are the same as defined in claim 1, in the presence of sulfuric acid, and then reacting the intermediate product and an acid or salt.

8. The process for preparing a N,N'-difluorodiazoniabicycloalkane salt of the formula (I):

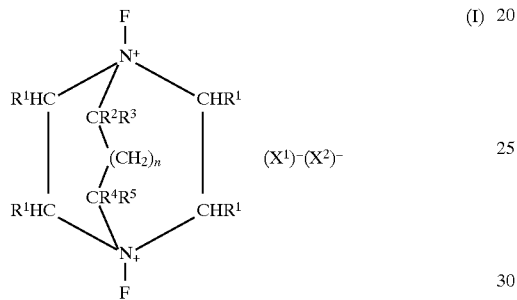

wherein $R^1$, $R^2$, $R^3$, $R^4$, $R^5$, n, $(X^1)^-$ and $(X^2)^-$ are the same as defined in claim 1, comprising the steps of reacting fluorine and a monoBrønsted acid salt of a diazabicycloalkane of the formula (III'):

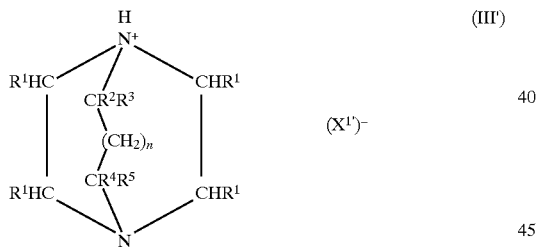

wherein $R^1$, $R^2$, $R^3$, $R^4$, $R^5$, n and $(X^{1'})^-$ are the same as defined in claims 1 and 4, in the presence or absence of a Brønsted acid, and then reacting the intermediate product with an acid or salt.

9. The process for preparing a N,N'-difluorodiazoniabicycloalkane salt of the formula (I):

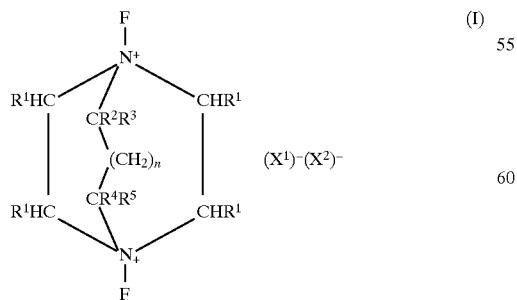

wherein $R^1$, $R^2$, $R^3$, $R^4$, $R^5$, n, $(X^1)^-$ and $(X^2)^-$ are the same as defined in claim 1, comprising the steps of reacting fluorine and a Brønsted acid salt of a diazabicycloalkane of the formula (IV'):

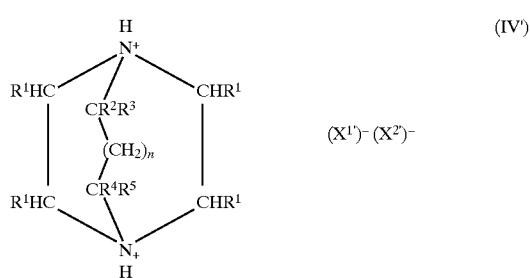

wherein $R^1$, $R^2$, $R^3$, $R^4$, $R^5$, n, $(X^{1'})^-$ and $(X^{2'})^-$ are the same as defined in claims 1 or 4, in the presence or absence of a base, and then reacting the intermediate product with an acid or salt.

10. The process for preparing a N,N'-difluorodiazoniabicycloalkane salt of the formula (I):

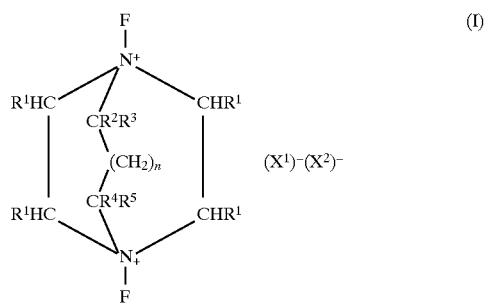

wherein $R^1$, $R^2$, $R^3$, $R^4$, $R^5$, n, $(X^1)^-$ and $(X^2)^-$ are the same as defined in claim 1, comprising the steps of reacting fluorine and a sulfate salt of a diazabicycloalkane of the formula (V):

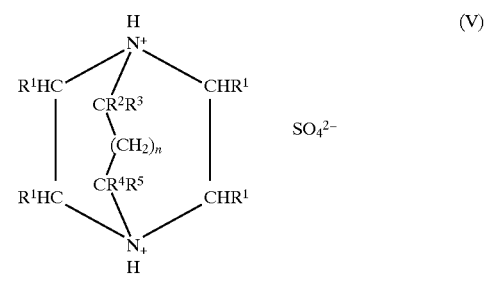

and/or the formula (V'):

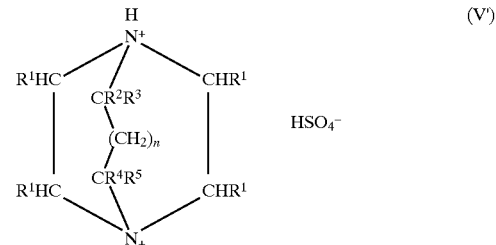

wherein $R^1$, $R^2$, $R^3$, $R^4$, $R^5$ and n are the same as defined in claim 1, and/or a di(hydrogensulfate) salt of a diazabicycloalkane of the formula (VI):

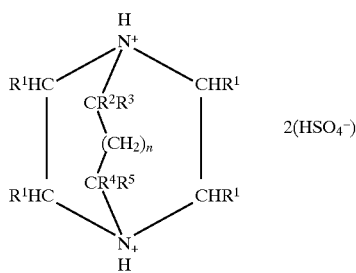

(VI)

wherein $R^1$, $R^2$, $R^3$, $R^4$, $R^5$ and n are the same as defined in claim 1, in the presence or absence of a base, and then reacting the intermediate product with an acid or salt.

11. The process according to claim 3, 9 or 10, wherein a base is an amine or an ammonium compound that is a base when the reaction is carried out in the presence of a base.

12. The process according to claims 3, 9, and 10, wherein the amount of a base is less than 1 mole per one mole of a Brønsted acid salt of a diazobicycloalkane of the formula (IV) or (IV'), a sulfate salt of a diazobicycloalkane of the formula (V) or (V'), or a di(hydrogensulfate) salt of a diazobicycloalkane of the formula (VI).

13. The process according to claim 1, wherein a solvent is used.

14. The process according to claim 13, wherein said solvent is at least one solvent selected from the group consisting of $C_2$–$C_5$ nitriles, $C_1$–$C_5$ halohydrocarbons, $C_1$–$C_5$ alcohols or halogenated alcohols and $C_1$–$C_4$ alkanoic or haloalkanoic acids.

15. The process according to claim 14, wherein said nitrile is acetonitrile or propionitrile; said halohydrocarbon is methylene chloride, chloroform, carbon tetrachloride, trichlorofluoromethane, bromotrofluoromethane, dichloroethne or trichlorotrifluoroethane; said alcohols or halogenated alcohol is methanol, ethanol, propanol, isopropanol, butanol, isobutanol, sec.-butanol, t-butanol, trifluoroethanol, trichloroethanol, pentafluoropropanol, tetrafluoropropanol, hexafluoroisopropanol, heptafluorobutanol, nonafluoro-t-butanol or octafluoropentanol; and said alkanoic or haloalkanoic acid is formic acid, acetic acid, trifluoroacetic acid, propionic acid, tetrafluoropropionic acid or pentafluoropropionic acid.

16. N,N'-Difluoro-1,4-diazoniabicyclo[2.2.2]octane di(hydrogensulfate) of the formula:

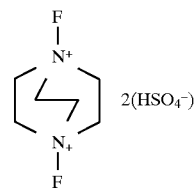

* * * * *

UNITED STATES PATENT AND TRADEMARK OFFICE
CERTIFICATE OF CORRECTION

PATENT NO. : 5,892,035
DATED : April 6, 1999
INVENTOR(S) : Umemoto et al.

It is certified that error appears in the above-identified patent and that said Letters Patent is hereby corrected as shown below:

On the cover page, column 1, please correct the title of the invention as follows:

[54] PROCESS FOR PREPARING N,N'-DIFLUORODIAZONIABICYCLOALKANE SALT, INTERMEDIATE THEREFOR, PRODUCT AND USE OF PRODUCT

Signed and Sealed this

First Day of February, 2000

*Attest:*

Q. TODD DICKINSON

*Attesting Officer*  *Acting Commissioner of Patents and Trademarks*